(12) United States Patent
Congreve et al.

(10) Patent No.: US 7,732,622 B2
(45) Date of Patent: *Jun. 8, 2010

(54) NAPHTHALENE DERIVATIVES

(75) Inventors: Miles Stuart Congreve, Cambridge (GB); Gerard Martin Paul Giblin, Welwyn (GB); Andrew McMurtrie Mason, Stevenage (GB); Neil Derek Miller, Stevenage (GB); Susan Roomans, Stevenage (GB); Ann Louise Walker, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/111,989

(22) Filed: Apr. 30, 2008

(65) Prior Publication Data
US 2008/0234358 A1 Sep. 25, 2008

Related U.S. Application Data

(62) Division of application No. 11/557,511, filed on Nov. 8, 2006, now abandoned, which is a division of application No. 10/467,487, filed as application No. PCT/GB02/00522 on Feb. 7, 2002, now Pat. No. 7,166,631.

(30) Foreign Application Priority Data

Feb. 9, 2001 (GB) ................................. 0103269.7

(51) Int. Cl.
C07D 209/60 (2006.01)
A61K 31/40 (2006.01)
(52) U.S. Cl. ...................................... 548/529; 514/411
(58) Field of Classification Search ................. 548/529; 514/411
See application file for complete search history.

(56) References Cited

U.S. PATENT DOCUMENTS

| 5,892,099 | A | 4/1999 | Maruyama et al. | |
| 6,043,275 | A | 3/2000 | Maruyama et al. | |
| 6,861,441 | B1 * | 3/2005 | Clayton et al. | 514/411 |
| 7,166,631 | B2 * | 1/2007 | Congreve et al. | 514/411 |
| 7,173,047 | B2 * | 2/2007 | Giblin et al. | 514/339 |

FOREIGN PATENT DOCUMENTS

| WO | 00/03980 | 1/2000 |
| WO | 00/18744 | 4/2000 |
| WO | 00/21532 | 4/2000 |
| WO | 01/10426 | 2/2001 |

OTHER PUBLICATIONS

Rufer et al., "New acylated 2-(4-aminophenyl)-propionic acids as potential antiinflammatory agents," European Journal of Medicinal Chemistry (1978), 13(2), 193-8. (cited in IDS).*
Rufer C., et al., "New acylated 2-(4-aminophenyl)-propionic acids as potential anti-inflammatory agents." Eur. J. Med. Chem.., 1978, V13, N2, pp. 193-198.

* cited by examiner

Primary Examiner—Rebecca L Anderson
Assistant Examiner—Robert Havlin
(74) Attorney, Agent, or Firm—Bonnie L. Deppenbrock

(57) ABSTRACT

A compound of formula (I)

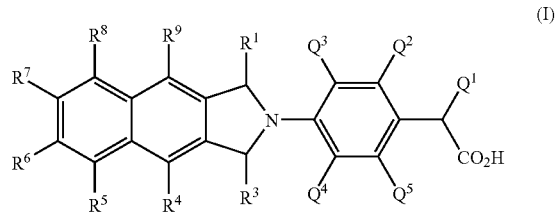

wherein
$R^1$ and $R^3$ are the same or different and represent =O, hydrogen, $C_{1-6}$alkyl, $C_{1-6}$dialkyl, =CHC$_1$-C$_5$alkyl, =S, or a 5- or 6-membered aryl;
$R^4$ to $R^9$ are the same or different and represent hydrogen, $C_{1-6}$alkoxy, OCF$_3$, OCH$_2$CF$_3$, O-cyclopropyl, OCH$_2$-cyclopropyl, $C_1$-$C_6$alkyl, S-alkyl, NR$_2^{10}$ where R$^{10}$ is hydrogen or $C_{1-6}$alkyl, halogen, NO$_2$, OH, CH$_2$OC$_1$-C$_6$alkyl, CH$_2$OH, or CF$_3$;
$Q^1$ is hydrogen, $C_{1-6}$alkyl, $C_{1-6}$dialkyl, $C_{1-6}$alkoxy, NHAc, NR$_2^{10}$ where R$^{10}$ is hydrogen or C$_{1-6}$alkyl, difluoro, fluoro, =O, or OH;
$Q^2$, $Q^3$, $Q^4$ and $Q^5$ are the same or different and represent hydrogen, $C_{1-6}$alkoxy, OCF$_3$, OCH$_2$CF$_3$, O-cyclopropyl, OCH$_2$-cyclopropyl, $C_1$-$C_6$alkyl, S-alkyl, NR$_2^{10}$ where R$^{10}$ is hydrogen or $C_{1-6}$alkyl, halogen, NO$_2$, OH, CH$_2$OC$_1$-C$_6$alkyl, CH$_2$OH, or a 5- or 6-membered aryl;
with the proviso that the compounds [4-(1-oxo-1,3-dihydro-2H-benzo[f]isoindol-2-yl)phenyl]-2-propionic acid, sodium salt and [4-(4,9-diethoxy-1-oxo-1,3-dihydro-2H-benzo[f]isoindol-2-yl)phenyl]acetic acid are excluded; and pharmaceutically acceptable derivatives thereof.

3 Claims, No Drawings

NAPHTHALENE DERIVATIVES

This application is a divisional of U.S. Ser. No. 11/557,511 filed on Nov. 8, 2006, now abandoned which is a divisional of U.S. Ser. No. 10/467,487 filed on May 10, 2004, now U.S. Pat. No. 7,166,631 which was filed pursuant to 35 U.S.C. §371 as a United States National Phase Application of International Application No. PCT/GB2002/00522 filed Feb. 7, 2002, which claims priority from GB 0103269.7 filed Feb. 9, 2001.

This invention relates to naphthalene derivatives, to processes for their preparation, to pharmaceutical compositions containing them and to their use in medicine.

The EP4 receptor is a 7-transmembrane receptor and its natural ligand is the prostaglandin $PGE_2$. $PGE_2$ also has affinity for the other EP receptors (types EP1, EP2 and EP3). The EP4 receptor is associated with smooth muscle relaxation, inflammation, lymphocyte differentiation, bone metabolism processes, allergic activities, promotion of sleep, renal regulation and gastric or enteric mucus secretion. We have now found a novel group of compounds which bind with high affinity to the EP4 receptor.

Compounds exhibiting EP4 binding activity have been described in, for example, WO00/18744, WO00/03980, WO00/15608, WO0016760, WO00/21532, WO98/55468, EP0855389 and EP0985663. GB2330307 describes the use of EP4 antagonists in the treatment of conditions with accelerated bone resorption. Derivatives of indoprofen, such as [4-(1-oxo-1,3-dihydro-2H-benzo[f]isoindol-2-yl)phenyl]-2-propionic acid, sodium salt shown below, have been described by Rufer et. al. In Eur. J. Med. Chem.—Chimica Therapeutica, 1978, 13, no 2, pg 193-198.

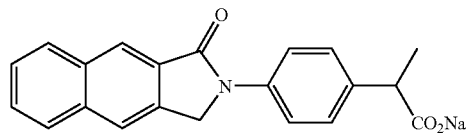

Accordingly, the present invention provides a compound of formula (I)

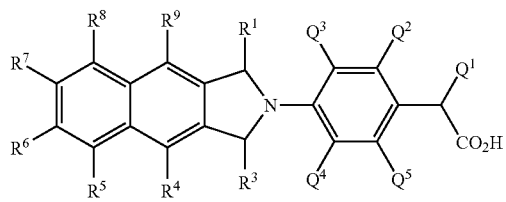

wherein
R$^1$ and R$^3$ are the same or different and represent =O, hydrogen, $C_{1-6}$alkyl, $C_{1-6}$dialkyl, =CHC$_1$-C$_5$alkyl, =S, or a 5- or 6-membered aryl;
R$^4$ to R$^9$ are the same or different and represent hydrogen, $C_{1-6}$alkoxy, $OCF_3$, $OCH_2CF_3$, O-cyclopropyl, $OCH_2$-cyclopropyl, $C_1$-$C_6$alkyl, S-alkyl, $NR_2^{10}$ where $R^{10}$ is hydrogen or $C_{1-6}$alkyl, halogen, $NO_2$, OH, $CH_2OC_1$-$C_6$alkyl, $CH_2OH$, or $CF_3$;
Q$^1$ is hydrogen, $C_{1-6}$alkyl, $C_{1-6}$dialkyl, $C_{1-6}$alkoxy, NHAc, $NR_2^{10}$ where $R^{10}$ is hydrogen or $C_{1-6}$alkyl, difluoro, fluoro, =O, or OH;
Q$^2$, Q$^3$, Q$^4$ and Q$^5$ are the same or different and represent hydrogen, $C_{1-6}$alkoxy, $OCF_3$, $OCH_2CF_3$, O-cyclopropyl, $OCH_2$-cyclopropyl, $C_1$-$C_6$alkyl, S-alkyl, $NR_2^{10}$ where $R^{10}$ is hydrogen or $C_{1-6}$alkyl, halogen, $NO_2$, OH, $CH_2OC_1$-$C_6$alkyl, $CH_2OH$, or a 5- or 6-membered aryl;
with the proviso that the compounds [4-(1-oxo-1,3-dihydro-2H-benzo[f]isoindol-2-yl)phenyl]-2-propionic acid, sodium salt and [4-(4,9-diethoxy-1-oxo-1,3-dihydro-2H-benzo[f]isoindol-2-yl)phenyl]acetic acid are excluded;

and pharmaceutically acceptable derivatives thereof.

By pharmaceutically acceptable derivative is meant any pharmaceutically acceptable salt, solvate or ester, or salt or solvate of such ester of the compounds of formula (I), or any other compound which upon administration to the recipient is capable of providing (directly or indirectly) a compound of formula (I) or an active metabolite or residue thereof.

It will be appreciated by those skilled in the art that the compounds of formula (I) may be modified to provide pharmaceutically acceptable derivatives thereof at any of the functional groups in the compounds, and that the compounds of formula (I) may be derivatised at more than one position.

It will be appreciated that, for pharmaceutical use, the salts referred to above will be the pharmaceutically acceptable salts, but other salts may find use, for example in the preparation of compounds of formula (I) and the pharmaceutically acceptable salts thereof.

Pharmaceutically acceptable salts include those described by Berge, Bighley and Monkhouse, J. Pharm. Sci., 1977, 66, 1-19. Suitable pharmaceutically acceptable salts of the compounds of formula (I) include acid addition salts formed with inorganic or organic acids, preferably inorganic acids, e.g. hydrochlorides, hydrobromides and sulphates. Further representative examples of pharmaceutically acceptable salts include those formed from acetic, maleic, fumaric, benzoic, ascorbic, pamoic, succinic, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids. Further representative examples of pharmaceutically acceptable salts include alkali metal salts, formed from the addition of alkali metal bases, such as alkali metal hydroxides e.g. sodium salts.

It will be appreciated that the compound of formula (I) may be produced in vivo by metabolism of a suitable prodrug. Such prodrugs may be for example physiologically acceptable metabolically labile esters of compounds of the general formula (I). These may be formed by esterification of the carboxylic acid group in the parent compound of general formula (I) with, where appropriate, prior protection of any other reactive groups present in the molecule followed by deprotection if required. Examples of such metabolically labile esters include $C_{1-4}$alkyl esters e.g. methyl ethyl or t-butyl esters esters, $C_{3-6}$ alkenyl esters e.g. allyl substituted or unsubstituted aminoalkyl esters (e.g. aminoethyl, 2-(N,N-diethylamino)ethyl, or 2-(4-morpholino)ethyl esters or acyloxyalkyl esters such as, acyloxymethyl or 1-acyloxyethyl e.g. pivaloyloxymethyl, 1-pivaloyloxyethyl, acetoxymethyl, 1-acetoxyethyl, 1-(1-methoxy-1-methyl)ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxy)carbonyloxyethyl or 1-(4-tetrahydropyranyl)carbonyloxyethyl.

As used herein, the term halogen atom includes fluorine, and more especially chlorine, bromine or iodine.

The term $C_{1-6}$alkyl, $C_{1-6}$alkoxy or =CHC$_{1-5}$alkyl as used herein includes straight chain and branched chain alkyl or alkoxy groups containing 1 to 6 carbon atoms, and in particular includes methyl, ethyl, n-propyl and i-propyl or methoxy, ethoxy, i-propoxy, n-propoxy, n-butyloxy or n-hexyloxy.

The term 5-membered aryl as used herein means an aryl selected from the following:

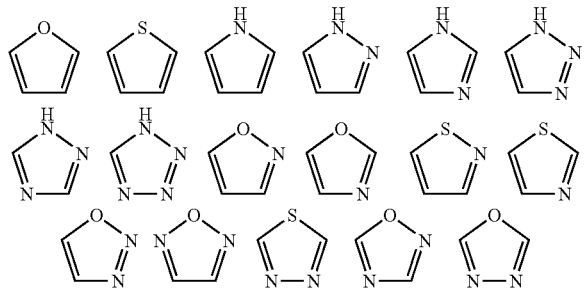

The term 6-membered aryl as used herein means an aryl selected from:

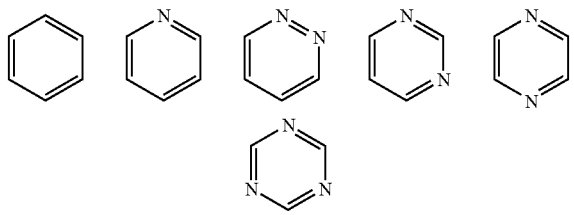

A preferred subgroup of compounds of formula (I) include the compounds wherein $R^1$ is =O or hydrogen;

$R^3$ is =O, hydrogen, $C_{1-6}$alkyl, $C_{1-6}$dialkyl, or a 5- or 6-membered aryl;

$R^4$ and $R^9$ are the same or different and represent hydrogen or $C_{1-6}$alkoxy;

$R^5$ and $R^8$ are hydrogen, or $CF_3$;

$R^6$ and $R^7$ are the same or different and represent hydrogen, $C_{1-6}$alkyl, $C_{1-6}$alkoxy, halogen, $NO_2$, or $CF_3$;

$Q^1$ is hydrogen, $C_{1-6}$alkyl, $C_{1-6}$alkoxy, NHAc, or $NR_2^{10}$ where $R^{10}$ is hydrogen or $C_{1-6}$alkyl;

$Q^2$, $Q^3$, $Q^4$ and $Q^5$ are the same or different and represent hydrogen, $C_{1-6}$alkyl, $C_{1-6}$alkoxy, halogen, or a 5- or 6-membered aryl;

with the proviso that the compounds [4-(1-oxo-1,3-dihydro-2H-benzo[f]isoindol-2-yl)phenyl]-2-propionic acid, sodium salt and [4-(4,9-diethoxy-1-oxo-1,3-dihydro-2H-benzo[f]isoindol-2-yl)phenyl]acetic acid are excluded;

and pharmaceutically acceptable derivatives thereof.

$R^1$ is preferably =O.

$R^3$ is aptly selected from methyl, dimethyl, or 2-furanyl. $R^3$ is preferably =O or hydrogen, and is more preferably hydrogen.

$R^4$ and $R^9$ are each suitably hydrogen, methoxy, ethoxy, i-propoxy, n-propoxy, n-butyloxy or n-hexyloxy. Suitably at least one of $R^4$ and $R^9$ represents $C_{1-6}$alkoxy when $Q^1$ is methyl. Preferably $R^4$ and $R^9$ are both $C_{1-6}$alkoxy, eg ethoxy.

$R^6$ and $R^7$ are suitably hydrogen, methyl, methoxy, chlorine, bromine, iodine, $NO_2$, or $CF_3$. Preferably $R^6$ and $R^7$ are both hydrogen.

$Q^1$ is suitably hydrogen, methyl, ethyl, NHAc, $NH_2$ or methoxy. $Q^1$ is preferably hydrogen.

$Q^2$, $Q^3$, $Q^4$ and $Q^5$ are each suitably hydrogen, methyl, methoxy, chlorine, bromine, iodine, 2-thiophenyl, 3-thiophenyl, 2-furanyl, 3-furanyl, or phenyl. Preferably $Q^2$, $Q^3$, $Q^4$ and $Q^5$ are all hydrogen.

A further preferred group of compounds of formula (I) are those wherein $R^1$ is =O; $R^3$ is methyl, dimethyl, 2-furanyl, preferably =O or hydrogen, and is more preferably hydrogen; $R^4$ and $R^9$ are each hydrogen, methoxy, ethoxy, i-propoxy, n-propoxy, n-butyloxy or n-hexyloxy, preferably $R^4$ and $R^9$ are both $C_{1-6}$alkoxy, eg ethoxy; $R^5$ and $R^8$ are hydrogen; $R^6$ and $R^7$ are hydrogen, methyl, methoxy, chlorine, bromine, iodine, $NO_2$, or $CF_3$, preferably $R^6$ and $R^7$ are both hydrogen; $Q^1$ is suitably hydrogen, methyl, ethyl, NHAc, $NH_2$ or methoxy, preferably hydrogen; $Q^2$, $Q^3$, $Q^4$ and $Q^5$ are each suitably hydrogen, methyl, methoxy, chlorine, bromine, iodine, 2-thiophenyl, 3-thiophenyl, 2-furanyl, 3-furanyl, or phenyl, preferably $Q^2$, $Q^3$, $Q^4$ and $Q^5$ are all hydrogen;

with the proviso that the compounds [4-(1-oxo-1,3-dihydro-2H-benzo[f]isoindol-2-yl)phenyl]-2-propionic acid, sodium salt and [4-(4,9-diethoxy-1-oxo-1,3-dihydro-2H-benzo[f]isoindol-2-yl)phenyl]acetic acid are excluded;

and pharmaceutically acceptable derivatives thereof.

It is to be understood that the present invention encompasses all isomers of the compounds of formula (I) and their pharmaceutically acceptable derivatives, including all geometric, tautomeric and optical forms, and mixtures thereof (e.g. racemic mixtures).

Preferred compounds of the present invention include:

[4-(4-methoxy-1-oxo-1,3-dihydro-2H-benzo[f]isoindol-2-yl)phenyl]acetic acid;

[4-(4,9-dimethoxy-1-oxo-1,3-dihydro-2H-benzo[f]isoindol-2-yl)phenyl]acetic acid;

[4-(4-methoxy-9-ethoxy-1-oxo-1,3-dihydro-2H-benzo[f]isoindol-2-yl)phenyl]acetic acid;

[4-(4-methoxy-9-propoxy-1-oxo-1,3-dihydro-2H-benzo[f]isoindol-2-yl)phenyl]acetic acid;

[4-(4-methoxy-9-isopropoxy-1-oxo-1,3-dihydro-2H-benzo[f]isoindol-2-yl)phenyl]acetic acid;

[4-(4-ethoxy-9-methoxy-1-oxo-1,3-dihydro-2H-benzo[f]isoindol-2-yl)phenyl]acetic acid;

[4-(4-ethoxy-9-propoxy-1-oxo-1,3-dihydro-2H-benzo[f]isoindol-2-yl)phenyl]acetic acid;

[4-(4-ethoxy-9-isopropoxy-1-oxo-1,3-dihydro-2H-benzo[f]isoindol-2-yl)phenyl]acetic acid;

[4-(4-ethoxy-1-oxo-1,3-dihydro-2H-benzo[f]isoindol-2-yl)phenyl]acetic acid;

[4-(4-propoxy-9-methoxy-1-oxo-1,3-dihydro-2H-benzo[f]isoindol-2-yl)phenyl]acetic acid;

[4-(4-propoxy-9-ethoxy-1-oxo-1,3-dihydro-2H-benzo[f]isoindol-2-yl)phenyl]acetic acid;

[4-(4,9-dipropoxy-1-oxo-1,3-dihydro-2H-benzo[f]isoindol-2-yl)phenyl]acetic acid;

[4-(9-isopropoxy-4-propoxy-1-oxo-1,3-dihydro-2H-benzo[f]isoindol-2-yl)phenyl]acetic acid;

[4-(4-propoxy-1-oxo-1,3-dihydro-2H-benzo[f]isoindol-2-yl)phenyl]acetic acid;

[4-(4-isopropoxy-9-methoxy-1-oxo-1,3-dihydro-2H-benzo[f]isoindol-2-yl)phenyl]acetic acid;

[4-(4-isopropoxy-9-ethoxy-1-oxo-1,3-dihydro-2H-benzo[f]isoindol-2-yl)phenyl]acetic acid;

[4-(4-isopropoxy-9-propoxy-1-oxo-1,3-dihydro-2H-benzo[f]isoindol-2-yl)phenyl]acetic acid;
[4-(4,9-di-isopropoxy-1-oxo-1,3-dihydro-2H-benzo[f]isoindol-2-yl)phenyl]acetic acid;
[4-(4-isopropoxy-1-oxo-1,3-dihydro-2H-benzo[f]isoindol-2-yl)phenyl]acetic acid;
[4-(9-methoxy-1-oxo-1,3-dihydro-2H-benzo[f]isoindol-2-yl)phenyl]acetic acid;
[4-(9-ethoxy-1-oxo-1,3-dihydro-2H-benzo[f]isoindol-2-yl)phenyl]acetic acid;
[4-(9-propoxy-1-oxo-1,3-dihydro-2H-benzo[f]isoindol-2-yl)phenyl]acetic acid;
[4-(9-isopropoxy-1-oxo-1,3-dihydro-2H-benzo[f]isoindol-2-yl)phenyl]acetic acid;
[4-(4,9-diethoxy-1,3-dioxo-1,3-dihydro-2H-benzo[f]isoindol-2-yl)phenyl]acetic acid;
[4-(4-methoxy-1,3-dioxo-1,3-dihydro-2H-benzo[f]isoindol-2-yl)phenyl]acetic acid;
[4-(4,9-dimethoxy-1,3-dioxo-1,3-dihydro-2H-benzo[f]isoindol-2-yl)phenyl]acetic acid;
[4-(4-methoxy-9-ethoxy-1,3-dioxo-1,3-dihydro-2H-benzo[f]isoindol-2-yl)phenyl]acetic acid;
[4-(4-methoxy-9-propoxy-1,3-dioxo-1,3-dihydro-2H-benzo[f]isoindol-2-yl)phenyl]acetic acid;
[4-(4-methoxy-9-isopropoxy-1,3-dioxo-1,3-dihydro-2H-benzo[f]isoindol-2-yl)phenyl]acetic acid;
[4-(4-ethoxy-9-propoxy-1,3-dioxo-1,3-dihydro-2H-benzo[f]isoindol-2-yl)phenyl]acetic acid;
[4-(4-ethoxy-9-isopropoxy-1,3-dioxo-1,3-dihydro-2H-benzo[f]isoindol-2-yl)phenyl]acetic acid;
[4-(4-ethoxy-1,3-dioxo-1,3-dihydro-2H-benzo[f]isoindol-2-yl)phenyl]acetic acid;
[4-(4,9-dipropoxy-1,3-dioxo-1,3-dihydro-2H-benzo[f]isoindol-2-yl)phenyl]acetic acid;
[4-(9-isopropoxy-4-propoxy-1,3-dioxo-1,3-dihydro-2H-benzo[f]isoindol-2-yl) phenyl]acetic acid;
[4-(4-propoxy-1,3-dioxo-1,3-dihydro-2H-benzo[f]isoindol-2-yl)phenyl]acetic acid;
[4-(4,9-di-isopropoxy-1,3-dioxo-1,3-dihydro-2H-benzo[f]isoindol-2-yl)phenyl]acetic acid;
[4-(4-isopropoxy-1,3-dioxo-1,3-dihydro-2H-benzo[f]isoindol-2-yl)phenyl]acetic acid;
[4-(4,9-diethoxy-1-oxo-1,3-dihydro-2H-benzo[f]isoindol-2-yl)phenyl]-2-propionic acid;
[4-(4,9-diethoxy-1-oxo-1,3-dihydro-2H-benzo[f]isoindol-2-yl)phenyl]-2-butyric acid;
[4-(4,9-diethoxy-1-oxo-1,3-dihydro-2H-benzo[f]isoindol-2-yl)phenyl]-2-(N-acetylamino)acetic acid;
[4-(4,9-diethoxy-1-oxo-1,3-dihydro-2H-benzo[f]isoindol-2-yl)phenyl]-2-aminoacetic acid;
[4-(4,9-diethoxy-1-oxo-1,3-dihydro-2H-benzo[f]isoindol-2-yl)phenyl]-2-methoxyacetic acid;
[4-(4,9-diethoxy-1-oxo-1,3-dihydro-2H-benzo[f]isoindol-2-yl)-3-methylphenyl]acetic acid;
[4-(4,9-diethoxy-1-oxo-1,3-dihydro-2H-benzo[f]isoindol-2-yl)-3-methoxyphenyl]acetic acid;
[4-(4,9-diethoxy-1-oxo-1,3-dihydro-2H-benzo[f]isoindol-2-yl)-3,5-dimethylphenyl]acetic acid;
[4-(4,9-diethoxy-1-oxo-1,3-dihydro-2H-benzo[f]isoindol-2-yl)-3-iodophenyl]acetic acid;
[3-chloro-4-(4,9-diethoxy-1-oxo-1,3-dihydro-2H-benzo[f]isoindol-2-yl)-phenyl]acetic acid;
[3-bromo-4-(4,9-diethoxy-1-oxo-1,3-dihydro-2H-benzo[f]isoindol-2-yl)-phenyl]acetic acid;
[4-(4,9-diethoxy-1-oxo-1,3-dihydro-2H-benzo[f]isoindol-2-yl)-2-methylphenyl]acetic acid;
[4-(4,9-diethoxy-1-oxo-1,3-dihydro-2H-benzo[f]isoindol-2-yl)-2-methoxyphenyl]acetic acid;
[2-chloro-4-(4,9-diethoxy-1-oxo-1,3-dihydro-2H-benzo[f]isoindol-2-yl)-phenyl]acetic acid;
[4-(4,9-diethoxy-1-oxo-1,3-dihydro-2H-benzo[f]isoindol-2-yl)-2-iodophenyl]acetic acid;
[2-bromo-4-(4,9-diethoxy-1-oxo-1,3-dihydro-2H-benzo[f]isoindol-2-yl)-phenyl]acetic acid;
[4-(6,7-dichloro-4,9-diethoxy-1-oxo-1,3-dihydro-2H-benzo[f]isoindol-2-yl)phenyl]acetic acid;
[4-(4,9-diethoxy-6-methyl-1-oxo-1,3-dihydro-2H-benzo[f]isoindol-2-yl)phenyl]acetic acid;
[4-(4,9-diethoxy-7-methyl-1-oxo-1,3-dihydro-2H-benzo[f]isoindol-2-yl)phenyl]acetic acid;
[4-(7-bromo-4,9-diethoxy-1-oxo-1,3-dihydro-2H-benzo[f]isoindol-2-yl)phenyl]acetic acid;
[4-(4,9-diethoxy-7-iodo-1-oxo-1,3-dihydro-2H-benzo[f]isoindol-2-yl)phenyl]acetic acid;
[4-(6-bromo-4,9-diethoxy-1-oxo-1,3-dihydro-2H-benzo[f]isoindol-2-yl)phenyl]acetic acid;
[4-(4,9-diethoxy-6-iodo-1-oxo-1,3-dihydro-2H-benzo[f]isoindol-2-yl)phenyl]acetic acid;
[4-(4,9-diethoxy-3,3-dimethyl-1-oxo-1,3-dihydro-2H-benzo[f]isoindol-2-yl)phenyl]acetic acid;
[4-(4,9-diethoxy-3-methyl-1-oxo-1,3-dihydro-2H-benzo[f]isoindol-2-yl)phenyl]acetic acid;
[4-(4,9-diethoxy-6-nitro-1-oxo-1,3-dihydro-2H-benzo[f]isoindol-2-yl)phenyl]acetic acid;
[4-(4,9-diethoxy-7-nitro-1-oxo-1,3-dihydro-2H-benzo[f]isoindol-2-yl)phenyl]acetic acid;
[4-(4,9-diethoxy-6-methoxy-1-oxo-1,3-dihydro-2H-benzo[f]isoindol-2-yl)phenyl]acetic acid;
[4-(4,9-diethoxy-7-methoxy-1-oxo-1,3-dihydro-2H-benzo[f]isoindol-2-yl)phenyl]acetic acid;
[4-(6-chloro-4,9-diethoxy-1-oxo-1,3-dihydro-2H-benzo[f]isoindol-2-yl)phenyl]acetic acid;
[4-(7-chloro-4,9-diethoxy-1-oxo-1,3-dihydro-2H-benzo[f]isoindol-2-yl)phenyl]acetic acid;
[4-(4,9-dibutoxy-1-oxo-1,3-dihydro-2H-benzo[f]isoindol-2-yl)phenyl]acetic acid;
[4-(4,9-dihexyloxy-1-oxo-1,3-dihydro-2H-benzo[f]isoindol-2-yl)phenyl]acetic acid;
[4-(4-hexyloxy-9-isopropoxy-1-oxo-1,3-dihydro-2H-benzo[f]isoindol-2-yl)phenyl]acetic acid;
[4-(9-hexyloxy-4-isopropoxy-1-oxo-1,3-dihydro-2H-benzo[f]isoindol-2-yl)phenyl]acetic acid;
[4-(4,9-dibutoxy-1,3-dioxo-1,3-dihydro-2H-benzo[f]isoindol-2-yl)phenyl]acetic acid;
[4-(4,9-dihexyloxy-1,3-dioxo-1,3-dihydro-2H-benzo[f]isoindol-2-yl)phenyl]acetic acid;
[4-(4-butoxy-9-isopropoxy-1,3-dioxo-1,3-dihydro-2H-benzo[f]isoindol-2-yl)phenyl]acetic acid;
[4-(4,9-diethoxy-1,3-dihydro-2H-benzo[f]isoindol-2-yl) phenyl]acetic acid;
[4-(9-ethoxy-4-isopropoxy-1-oxo-1,3-dihydro-2H-benzo[f]isoindol-2-yl)phenyl]acetic acid;

and pharmaceutically acceptable derivatives thereof.

Particularly preferred compounds according to the invention are:
[4-(4,9-dimethoxy-1-oxo-1,3-dihydro-2H-benzo[f]isoindol-2-yl)phenyl]acetic acid;
[4-(4,9-diethoxy-1,3-dihydro-2H-benzo[f]isoindol-2-yl) phenyl]acetic acid;
[4-(4,9-di-isopropoxy-1-oxo-1,3-dihydro-2H-benzo[f]isoindol-2-yl)phenyl]acetic acid;

[4-(4,9-dipropoxy-1-oxo-1,3-dihydro-2H-benzo[f]isoindol-2-yl)phenyl]acetic acid;
[4-(4,9-dibutoxy-1-oxo-1,3-dihydro-2H-benzo[f]isoindol-2-yl)phenyl]acetic acid;
[4-(4,9-dihexyloxy-1-oxo-1,3-dihydro-2H-benzo[f]isoindol-2-yl)phenyl]acetic acid;
[4-(4-ethoxy-9-isopropoxy-1-oxo-1,3-dihydro-2H-benzo[f]isoindol-2-yl)phenyl]acetic acid;
[4-(9-ethoxy-4-isopropoxy-1-oxo-1,3-dihydro-2H-benzo[f]isoindol-2-yl)phenyl]acetic acid;
[4-(9-isopropoxy-4-propoxy-1-oxo-1,3-dihydro-2H-benzo[f]isoindol-2-yl)phenyl]acetic acid;
[4-(4-isopropoxy-9-propoxy-1-oxo-1,3-dihydro-2H-benzo[f]isoindol-2-yl)phenyl]acetic acid;
[4-(4-hexyloxy-9-isopropoxy-1-oxo-1,3-dihydro-2H-benzo[f]isoindol-2-yl)phenyl]acetic acid;
[4-(9-hexyloxy-4-isopropoxy-1-oxo-1,3-dihydro-2H-benzo[f]isoindol-2-yl)phenyl]acetic acid;
[4-(4-methoxy-1-oxo-1,3-dihydro-2H-benzo[f]isoindol-2-yl)phenyl]acetic acid;
[4-(4,9-diethoxy-1,3-dioxo-1,3-dihydro-2H-benzo[f]isoindol-2-yl)phenyl]acetic acid;
[4-(4,9-di-isopropoxy-1,3-dioxo-1,3-dihydro-2H-benzo[f]isoindol-2-yl)phenyl]acetic acid;
[4-(4,9-dipropoxy-1,3-dioxo-1,3-dihydro-2H-benzo[f]isoindol-2-yl)phenyl]acetic acid;
[4-(4,9-dibutoxy-1,3-dioxo-1,3-dihydro-2H-benzo[f]isoindol-2-yl)phenyl]acetic acid;
[4-(4,9-dihexyloxy-1,3-dioxo-1,3-dihydro-2H-benzo[f]isoindol-2-yl)phenyl]acetic acid;
[4-(4-ethoxy-9-isopropoxy-1,3-dioxo-1,3-dihydro-2H-benzo[f]isoindol-2-yl)phenyl]acetic acid;
[4-(9-isopropoxy-4-propoxy-1,3-dioxo-1,3-dihydro-2H-benzo[f]isoindol-2-yl)phenyl]acetic acid;
[4-(4-butoxy-9-isopropoxy-1,3-dioxo-1,3-dihydro-2H-benzo[f]isoindol-2-yl)phenyl]acetic acid;

and pharmaceutically acceptable derivatives thereof.

It is to be understood that the present invention covers all combinations of particular and preferred groups as described herein above.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

The compounds of the invention bind to the EP4 receptor and are therefore useful in treating EP4 receptor mediated diseases.

In view of their ability to bind to the EP4 receptor, the compounds of the invention are useful in the treatment of the disorders that follow. Thus, the compounds of formula (I) are useful as analgesics. For example they are useful in the treatment of chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of the invention are particularly useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of formula (I) are also useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome pigeon fancier's disease, farmer's lung, COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds of formula (I) are also useful in the treatment of immunological diseases such as autoimmune diseases, immunological deficiency diseases or organ transplantation. The compounds of formula (I) are also effective in increasing the latency of HIV infection.

The compounds of formula (I) are also useful in the treatment of diseases of abnormal platelet function (e.g. occlusive vascular diseases).

The compounds of formula (I) are also useful for the preparation of a drug with diuretic action.

The compounds of formula (I) are also useful in the treatment of impotence or erectile dysfunction.

The compounds of formula (I) are also useful in the treatment of bone disease characterised by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis. In a further aspect compounds of formula (I) may be useful in inhibiting bone resorption and/or promoting bone generation.

The compounds of formula (I) are also useful for attenuating the hemodynamic side effects of NSAIDs and COX-2 inhibitors.

The compounds of formula (I) are also useful in the treatment of cardiovascular diseases such as hypertension or myocardiac ischemia; functional or organic venous insufficiency; varicose therapy; haemorrhoids; and shock states associated with a marked drop in arterial pressure (e.g. septic shock).

The compounds of formula (I) are also useful in the treatment of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of formula (I) are also useful in the treatment of neuroprotection and in the treatment of neurodegeneration following stroke, cardiac arrest, pulmonary bypass, traumatic brain injury, spinal cord injury or the like.

The compounds of formula (I) are also useful in the treatment of tinnitus.

The compounds of formula (I) are also useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

The compounds of formula (I) are also useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of formula (I) are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

It is to be understood that reference to treatment includes both treatment of established symptoms and prophylactic treatment, unless explicitly stated otherwise.

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by the action of $PGE_2$ at EP4 receptors.

According to a further aspect of the invention, we provide a method of treating a human or animal subject suffering from a condition which is mediated by the action of $PGE_2$ at EP4 receptors which comprises administering to said subject an effective amount of a compound of formula (I) or a pharmaceutically acceptable derivative thereof.

According to a further aspect of the invention we provide a method of treating a human or animal subject suffering from a pain, inflammatory, immunological, bone, neurodegenerative or renal disorder, which method comprises administering to said subject an effective amount of a compound of formula (I) or a pharmaceutically acceptable derivative thereof.

According to another aspect of the invention, we provide the use of a compound of formula (I) or a pharmaceutically acceptable derivative thereof for the manufacture of a therapeutic agent for the treatment of a condition which is mediated by the action of $PGE_2$ at EP4 receptors.

According to another aspect of the invention we provide the use of a compound of formula (I) or a pharmaceutically acceptable derivative thereof for the manufacture of a therapeutic agent for the treatment or prevention of a condition such as a pain, inflammatory, immunological, bone, neurodegenerative or renal disorder.

The compounds of formula (I) and their pharmaceutically acceptable derivatives are conveniently administered in the form of pharmaceutical compositions. Such compositions may conveniently be presented for use in conventional manner in admixture with one or more physiologically acceptable carriers or excipients.

Thus, in another aspect of the invention, we provide a pharmaceutical composition comprising a compound of formula (I) or a pharmaceutically acceptable derivative thereof adapted for use in human or veterinary medicine.

While it is possible for the compounds of formula (I) or a pharmaceutically acceptable derivative thereof to be administered as the raw chemical, it is preferable to present it as a pharmaceutical formulation. The formulations of the present invention comprise the compounds of formula (I) or a pharmaceutically acceptable derivative thereof together with one or more acceptable carriers or diluents thereof and optionally other therapeutic ingredients. The carrier(s) must be "acceptable" in the sense of being compatible with the other ingredients of the formulation and not deleterious to the recipient thereof.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compound of formula (I) or a pharmaceutically acceptable acid addition salt thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

The EP4 receptor compounds for use in the instant invention may be used in combination with other therapeutic agents, for example COX-2 inhibitors, such as celecoxib, rofecoxib, valdecoxib or parecoxib; 5-lipoxygenase inhibitors; NSAID's, such as diclofenac, indomethacin, nabumetone or ibuprofen; leukotriene receptor antagonists; DMARD's such as methotrexate; adenosine A1 receptor agonists; sodium channel blockers, such as lamotrigine; NMDA receptor modulators, such as glycine receptor antagonists; gabapentin and related compounds; tricyclic antidepressants such as amitriptyline; neurone stabilising antiepileptic drugs; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; EP1 receptor ligands; EP2 receptor ligands; EP3 receptor ligands; EP1 antagonists; EP2 antagonists and EP3 antagonists. When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease, the dose of each compound may differ from that when the compound is used alone. Appropriate doses will be readily appreciated by those skilled in the art.

A proposed daily dosage of compounds of formula (I) or their pharmaceutically acceptable salts for the treatment of man is from 0.01 to 10 mg/kg body weight per day and more particularly 0.1 to 3 mg/kg body weight per day, calculated as the free base, which may be administered as a single or divided dose, for example one to four times per day The dose range for adult human beings is generally from 8 to 1000 mg/day, such as from 20 to 800 mg/day, preferably 35 to 200 mg/day, calculated as the free base.

The precise amount of the compounds of formula (I) administered to a host, particularly a human patient, will be the responsibility of the attendant physician. However, the dose employed will depend on a number of factors including the age and sex of the patient, the precise condition being treated and its severity, and the route of administration.

The present invention provides a process for preparing compounds of formula (I) and pharmaceutically acceptable derivatives thereof.

Compounds of formula (I) and pharmaceutically acceptable derivatives thereof may be prepared by any method known in the art for the preparation of compounds of analogous structure.

Suitable methods for the preparation of compounds of formula (I) and pharmaceutically acceptable derivatives thereof are described below and form a further aspect of the invention. In the formulae that follow, $R^1$ to $R^{10}$ and $Q^1$-$Q^5$ are as defined in formula (I) above unless otherwise stated.

According to a first process (A), compounds of formula (I), where $R^1$ and $R^3$ are both =O and $R^4$ and $R^9$ are the same or different and represent $C_{1-6}$alkoxy, may be prepared by reacting a compound of formula (II)

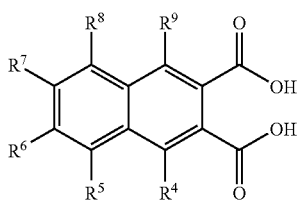

with a 4-aminophenylacetic acid of formula (III)

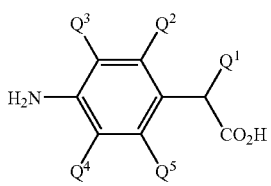

in glacial acetic acid at elevated temperature.

According to another process (B) compounds of formula (I), where one of $R^1$ and $R^3$ is =O and the other is hydrogen and $R^4$ and $R^9$ are the same or different and represent $C_{1-6}$alkoxy, may be prepared by reducing a compound of formula (IV)

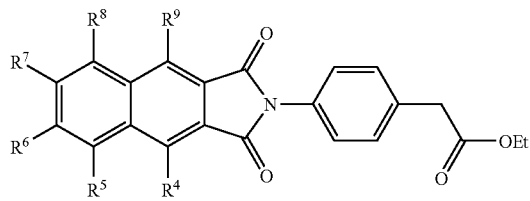

with a suitable reducing agent, followed by separation of isomers and deprotection (eg. with aqueous base at elevated temperature). Suitable reducing agents include zinc in acetic acid at elevated temperature and sodium borohydride in methanol followed by trifluoroacetic acid (TFA) and triethylsilane.

According to another process (C) compounds of formula (I), where one of $R^1$ and $R^3$ is =O and the other is hydrogen and $R^4$ and $R^9$ are the same or different and represent $C_{1-6}$alkoxy, may be prepared by reacting a compound of formula (V)

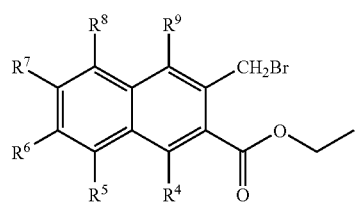

with a 4-aminophenylacetic acid of formula (III) as defined above in the presence of triethylamine and dimethylformamide, followed by deprotection (eg. using acetic acid at elevated temperature).

According to a further process (D) compounds of formula (I), where one of $R^1$ and $R^3$ is =O and the other is hydrogen and one of $R^4$ and $R^9$ is $C_{1-6}$alkoxy, may be prepared by reacting a compound of formula (VI)

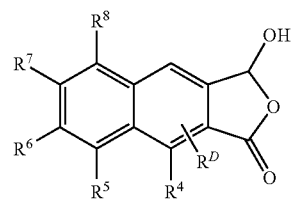

where $R^D$ is in the -4 or -9 position and is $C_{1-6}$ alkoxy, with a 4-aminophenylacetate of formula (VII)

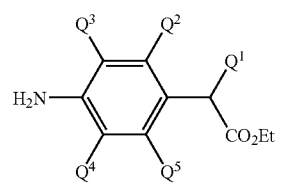

in the presence of sodium triacetoxyborohydride in a suitable solvent, such as dichloromethane, followed by deprotection (eg. with aqueous base at elevated temperature).

According to a further process (E) compounds of formula (I), where $R^1$ and $R^3$ are both hydrogen and $R^4$ and $R^9$ are the same or different and represent $C_{1-6}$ alkoxy, may be prepared by reacting a compound of formula (VIII)

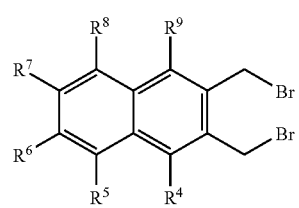

with a 4-aminophenylacetate of formula (VII) as described above in a suitable solvent, such as dimethylformamide, at elevated temperature followed by deprotection (eg. using aqueous base such as lithium hydroxide in aqueous tetrahydrofuran).

According to a further process (F) compounds of formula (I), where $R^3$ is =CHC$_{1-5}$alkyl, may be prepared by reacting a compound of formula (IV) as defined above with a Grignard reagent $C_1$-$C_6$alkyl-MgBr under conventional conditions, followed by separation of isomers and deprotection (eg. with aqueous base at elevated temperature).

According to a further process (G) compounds of formula (I), where $R^3$ is $C_{1-6}$dialkyl, may be prepared by reacting a compound of formula (IX)

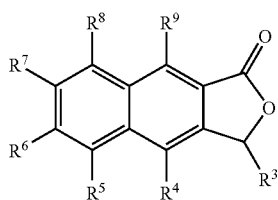

with a 4-aminophenylacetate of formula (VII) as defined above in the presence of aluminium trichloride, followed by deprotection (eg. with aqueous base at elevated temperature).

According to a further process (H) compounds of formula (I) prepared according to processes (A) to (G) may be converted into other compounds of formula (I) using conventional procedures. For example, compounds of formula (I) where $R^3$ is $C_{1-6}$alkyl, may be prepared by reducing a compound of formula (I) where $R^3$ is $=CHC_{1-5}$alkyl, protected at the carboxyl group, with a suitable reducing agent, such as hydrogen in the presence of a palladium on carbon catalyst, followed by deprotection (eg. with aqueous base at elevated temperature). Also, compounds of formula (I) where $R^3$ is $=O$ may be converted into compounds of formula (I) where $R^3$ is $=S$ by conventional methods, for example using Lawesson's reagent.

Compounds of formulae (II) to (IX) may be prepared by any method known in the art for the preparation of compounds of analogous structure.

Compounds of formula (II) may, for example be prepared according to Scheme 1 that follows.

Compounds of formula (IV) may be prepared by reacting compounds of formula (II) with a 4-aminophenylacetate of formula (VII) as defined above in the presence of acetic acid.

Compounds of formula (V) may, for example be prepared according to Scheme 2 that follows.

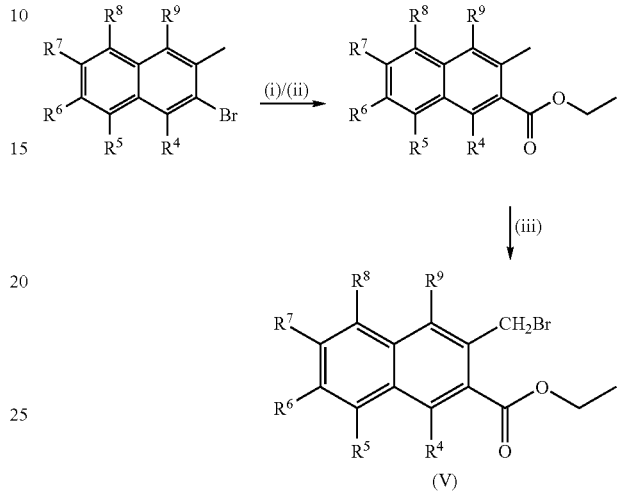

(i) n-BuLi, THF, -78° C.,
(ii) ClCO$_2$Et;
(iii) NBS, dibenzoyl peroxide, CCl$_4$, hv Compounds of formula (VI) may, for example, be prepared according to Scheme 3 that follows.

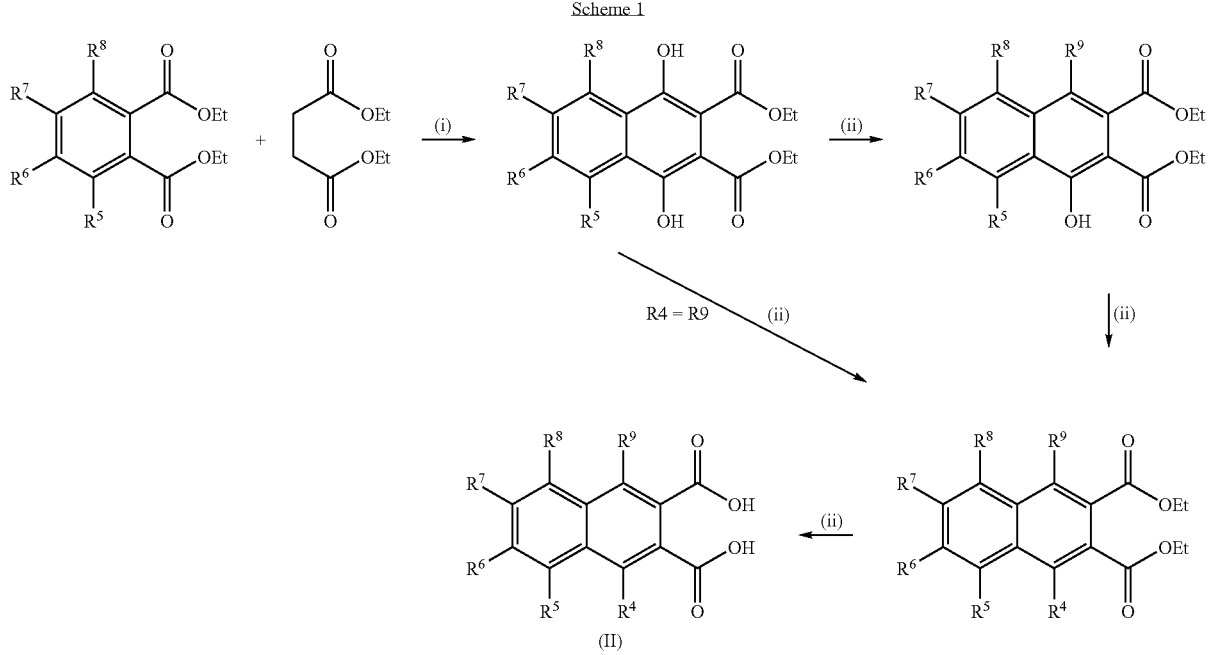

(i) NaOEt, EtOH;
(ii) C$_{1-6}$alkyl-hal, K$_2$CO$_3$, Acetone;
(iii) 2N NaOH, EtOH.

Scheme 3

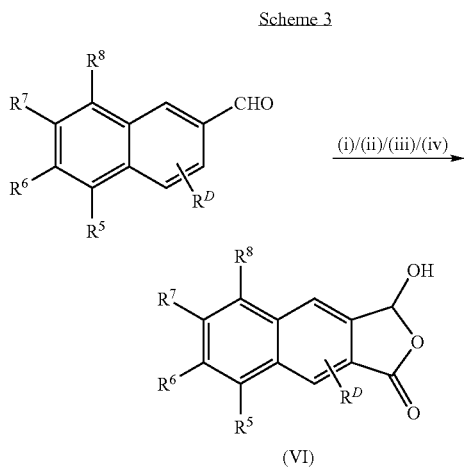

(i) (CH₃)₂N(CH₂)₂NHCH₃/n-BuLi/THF;
(ii) n-BuLi;
(iii) CO₂;
(iv) H₃O⁺

Compounds of formula (VIII) may be prepared, for example, by reacting a compound of formula (X)

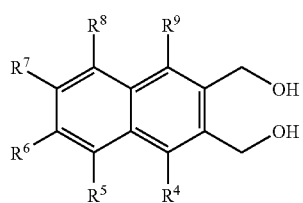

with phosphorous tribromide in an ether solvent, for example a mixture of diethyl ether and tetrahydrofuran.

Compounds of formula (IX) may be prepared by reacting a compound of formula (XI) with a Grignard reagent $R^3$—MgBr under conventional conditions.

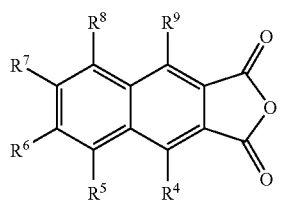

Compounds of formulae (III) and (VII) may be prepared according to methods known in the art for the preparation of analogous compounds, for example, compounds where $Q^1$ is methyl may be prepared by the method of Takahashi, I et al. Heterocycles (1996), 43(11), 2343-2346; compounds where $Q^1$ is ethyl may be prepared by the method of Kirschenheuter, Gary P et al. in EP465802; compounds where $Q^1$ is NHAc may be prepared by the method described in U.S. Pat. No. 3,479,339; compounds where $Q^1$ is NH₂ may be prepared by the method of Herbert, Richard B et al. J. Chem. Soc., Perkin Trans.1 (1992), (1), 109-13; compounds where $Q^1$ is MeO may be prepared from the corresponding nitro compounds prepared by the method of Tomioka, Hideo et al. J. Am. Chem. Soc. (1990), 112(21), 7692-702; compounds where $Q^2$ is Me or $Q^3$ is Cl may be prepared by the method described in U.S. Pat. No. 3,860,639 (Schultz, Everett M.); compounds where $Q^2$ is MeO may be prepared by the method of Nannini, G et al, Arzneim.-Forsch. (1973), 23(8), 1090-100 by hydrolysis of the ethyl ester; compounds where $Q^2$ is Cl may be prepared by the method of Atkinson, Joseph G et al. Tet Lett. (1979), (31), 2857-60 by reduction of the corresponding nitro compound; compounds where $Q^2$ is I may be prepared by the method of Sindelar, Karel et al. Collect. Czech. Chem. Commun. (1978), 43(2), 471-97 by reduction of the corresponding nitro compound; compounds where $Q^2$ is Br may be prepared by the method of Sindelar, Karel et al. Collect. Czech. Chem. Commun. (1978), 43(2), 471-97; compounds where $Q^3$ is Me may be prepared by the method of Borck, Joachim et al. in ZA 6804711; compounds where $Q^3$ is MeO may be prepared by the method of Gallacher, Gerard et al. Biorg. Amines (1995), 11(1), 49-62 by reduction of the corresponding nitro compound; compounds where $Q^3$ is I may be prepared by the method of Boehm, Marcus F et al. J. Chem. Soc., Chem. Commun. (1991), (1), 52-3; compounds where $Q^3$ is Br may be prepared by the method of Figala, Georg et al. in DE 2746067; compounds where $Q^3$ and $Q^4$ are Me may be prepared by the method of Yost, Yul et al. Org. Prep. Proced. Int. (1985), 17(4-5), 239-49 from the corresponding benzoic acid using the Arndt-Eistert reaction.

Certain intermediates described above are novel compounds, and it is to be understood that all novel intermediates herein form further aspects of the present invention. Compounds of formula (II), (V), (VI), (VIII) and (IX) are key intermediates and represent a particular aspect of the invention. Certain intermediates, such as compounds of formula (IV), may be prodrugs of compounds of formula (I).

Conveniently, compounds of the invention are isolated following work-up in the form of the free base. Pharmaceutically acceptable acid addition salts of the compounds of the invention may be prepared using conventional means.

Solvates (e.g. hydrates) of a compound of the invention may be formed during the work-up procedure of one of the aforementioned process steps.

The following Examples which should not be construed as constituting a limitation thereto are provided to illustrate the invention.

¹H NMR spectra were obtained at 400 MHz on a Bruker DPX400 spectrophotometer. J values are given in Hz. Mass spectra were obtained on a Micromass series II MS (electrospray positive or negative). Where HPLC retention times are given as a characterisation of intermediates or Examples this refers to an HP 1050 or a HP1100 running a 5.5 minute Gradient:
Eluents: A—0.1% V/V Formic Acid+10 mmol Ammonium Acetate
B—95% MeCN+0.05% V/V Formic Acid
Flow rate: 3 ml/min
Column: 3.3 cm×4.6 mm internal diameter, 3 μm ABZ+ PLUS
Injection Volume: 5 μl
Temperature: Room temperature.
Gradient:

| Time | % A | % B |
| --- | --- | --- |
| 0.00 | 100 | 0.00 |
| 0.70 | 100 | 0.00 |

-continued

| Time | % A | % B |
|------|-----|-----|
| 4.40 | 0.00 | 100 |
| 5.30 | 0.00 | 100 |
| 5.50 | 100 | 0.00 |

Intermediate 1

Ethyl 1,4-dihydroxy-2,3-naphthalenedicarboxylate

Sodium (60 g, 2.6 mol) was dissolved in ethanol (1.2 L) and the mixture was cooled to 40° C. Diethylphthalate (960 ml, 4.83 mol) was added and the mixture heated under nitrogen until the temperature reached 115° C. Diethyl succinate (211.3 g, 1.21 mol) was added dropwise over 45 min. The reaction was heated at 115° C. for a further 45 min, cooled to room temperature and poured onto water (1.2 L). Ethyl acetate (1 L) was added and stirred, the layers were separated and the organics were extracted with sodium hydroxide solution (2N, 1 L). The combined aqueous was acidified to pH 3 and the mixture extracted with ethyl acetate (2×1 L). The combined organics were washed with a saturated solution of sodium hydrogen carbonate (2×1.5 L), then brine, dried ($MgSO_4$), filtered and the solvent evaporated under vacuum. The residue was purified using a 2.5 kg Biotage column eluting with 5% ethyl acetate/hexane to give ethyl 1,4-dihydroxy-2,3-naphthalenedicarboxylate as a white solid, (60 g, 16%).

$\delta H$ $CDCl_3$ 10.44, (2H, s), 8.34, (2H, m), 7.68, (2H, m), 4.37, (4H, q), 1.37, (6H, t).

Intermediate 2

Ethyl 1,4-diethoxy-2,3-naphthalenedicarboxylate

Ethyl 1,4-dihydroxy-2,3-naphthalenedicarboxylate (30 g, 98.6 mmol) and potassium carbonate (150 g, 1.09 mmol) were stirred in acetone (600 ml) under nitrogen. Iodoethane (150 g, 0.96 mol) was added and the mixture was stirred at reflux overnight. The reaction was cooled, diluted with ethyl acetate and filtered. The filtrate was evaporated to leave a brown oil, which was dissolved in toluene and washed with potassium hydroxide solution (5%, 150 ml) and brine. Drying over magnesium sulphate and evaporation of the solvent gave a yellow solid. Purification using an 800 g Biotage column gave ethyl 1,4-diethoxy-2,3-naphthalenedicarboxylate as a white solid (32 g, 90%).

$\delta H$ $CDCl_3$ 8.16, (2H, m), 7.60, (2H, m), 4.40, (4H, q), 4.18, (4H, q), 1.50, (6H, t), 1.40, (6H, t).

Intermediate 3

1,4-Diethoxy-2,3-naphthalenedicarboxylic acid

Ethyl 1,4-diethoxy-2,3-naphthalenedicarboxylate (32 g, 89 mmol) was added to a solution of sodium hydroxide (20 g) in ethanol (200 ml) and water (40 ml) and stirred for 1.5 h at 60° C. The reaction was cooled and the thick white suspension was filtered. The solid was dissolved in a mixture of ethyl acetate (200 ml) and water (800 ml). The layers were separated and the aqueous was acidified with hydrochloric acid (2M, 120 ml). The aqueous was extracted with ethyl acetate (2×) and the combined organics were dried ($MgSO_4$). Evaporation of the solvent under vacuum gave 1,4-diethoxy-2,3-naphthalenedicarboxylic acid as a white solid (25 g, 92%).

$\delta H$ [$^2H_6$]-DMSO 13.26, (2H, s), 8.15, (2H, m), 7.72, (2H, m), 4.13, (4H, q), 1.42, (6H, t).

Intermediate 4

1,4-Diethoxy-2,3-naphthalenedicarboxylic anhydride 1,4-Diethoxy-2,3-naphthalenedicarboxylic acid (25 g, 82 mmol) was added to a solution of thionyl chloride (23.3 g) in chloroform (150 ml) and stirred at reflux for 1 h. The resulting solution was cooled and evaporated to dryness. Further chloroform was added and evaporation repeated to give 1,4-diethoxy-2,3-naphthalenedicarboxylic anhydride as a yellow solid (23.3 g, 99%).

$\delta H$ [$^2H_6$]-DMSO 8.42, (2H, m), 7.93, (2H, m), 4.53, (4H, q), 1.46, (6H, t).

Intermediate 5

Ethyl[4-(4,9-diethoxy-1,3-dioxo-1,3-dihydro-2H-benzo[f]isoindol-2-yl)phenyl]acetate 1,4-Diethoxy-2,3-naphthalenedicarboxylic anhydride (23.3 g, 81.5 mmol) and ethyl (4-aminophenyl)acetate (14.8 g, 82 mmol) were refluxed under nitrogen in acetic acid (160 ml) overnight. The mixture was cooled to room temperature and poured into water (1 L). The white solid was filtered, washed with water and dissolved in dichloromethane (800 ml). The solution was washed with water, brine and dried ($MgSO_4$) and the solvent evaporated under vacuum to give ethyl[4-(4,9-diethoxy-1,3-dioxo-1,3-dihydro-2H-benzo[f]isoindol-2-yl)phenyl]acetate as an off-white solid, 33 g, 96%.

$\delta H$ [$^2H_6$]-DMSO 8.40, (2H, m), 7.87, (2H, m), 7.42, (4H, s), 4.47, (4H, q), 4.12, (2H, q), 3.76, (2H, s), 1.45, (6H, t), 1.21, (3H, t).

Intermediate 6

3-Hydroxy-4-methoxynaphtho[2,3-c]furan-1(3H)-one

N,N,N'-Trimethylethylene diamine (0.82 ml, 6.3 mmol) was dissolved in tetrahydrofuran (16 ml) and cooled to −20° C. n-Butyl lithium (1.6M in hexanes, 3.9 ml, 6.24 mmol) was added and the reaction stirred at −20° C. for 15 min. 1-Methoxy-2-naphthaldehyde (0.96 g, 5.9 mmol) was added followed by n-butyl lithium (1.6M in hexanes, 11.25 ml, 18 mmol) and the reaction stirred at 25° C. for 3 h. Solid carbon dioxide was added and the reaction left until the excess carbon dioxide had sublimed. Stirring continued for 15 min before addition of hydrochloric acid (2N, 50 ml). The mixture was extracted with dichloromethane (50 ml, ×3). The combined extracts were dried ($MgSO_4$) and the solvent evaporated under vacuum. The oily residue was preabsorbed onto silica and purified by SPE (silica, 10 g) eluting with an ethyl acetate/cyclohexane gradient to give 3-hydroxy-4-methoxynaphtho[2,3-c]furan-1(3H)-one (50 mg, 3.7%).

$\delta H$ [$^2H_6$]-DMSO 8.28, (2H, m), 8.18, (2H, m), 7.70, (2H, m), 7.16, (1H, s), 4.27, (3H, s).

Intermediate 7

Ethyl 1,4-dimethoxy-2-methylnaphthalene-3-carboxylate n-Butyl lithium (1.6M in hexanes, 4.1 ml, 6.56 mmol) was added dropwise to 2-bromo-1,4-dimethoxy-3-methylnaphthalene (1.537 g, 5.47 mmol) in tetrahydrofuran (30 ml) at −50° C. The reaction was stirred for 30 min at −50° C. before dropwise addition of ethyl chloroformate (1 ml, 10.46 mmol). The reaction was allowed to warm to 0° C. over 18 h quenched by addition of hydrochloric acid (2N) and extracted with ethyl acetate. The extract was dried ($Na_2SO_4$) and the solvent evaporated under vacuum. The residue was purified by SPE (silica, 10 g) eluting with 10% ethyl acetate in cyclohexane to give ethyl 1,4-dimethoxy-2-methylnaphthalene-3-carboxylate (1.33 g, 89%).

δH $CDCl_3$ 8.08, (2H, d), 7.53, (2H, m), 4.48, (2H, q), 3.99, (3H, s), 3.88, (3H, s), 2.38, (3H, s), 1.44, (3H, t).

Intermediate 8

2,3-Bis(bromomethyl)-1,4-diethoxy-naphthalene

[1,4-Diethoxy-3-(hydroxymethyl)-2-naphthyl]methanol (92 mg, 0.33 mmol) was dissolved in a mixture of diethyl ether (1.5 ml) and tetrahydrofuran (2 ml) under nitrogen at 0° C. and phosphorus tribromide (0.035 ml, 0.35 mmol) was added dropwise. The reaction was allowed to warm to ambient temperature and stirred for 4 h before quenching with ice. The reaction mixture was extracted with ethyl acetate (3×5 ml) and the combined organic extracts dried over magnesium sulphate. The solvent was removed in vacuo, and the residue purified by SPE cartridge (silica), gradient elution cyclohexane to 75% cyclohexane/dichloromethane, to give 2,3-bis(bromomethyl)-1,4-diethoxy-naphthalene as a white solid (92 mg, 70%).

δH $CDCl_3$ 8.07 (2H, dd, J=6.5, 3.2), 7.54 (2H, dd, J=6.5, 3.2), 5.02 (4H, s), 4.21 (4H, q, J=7.0), 1.60 (6H, t, J=7.0); LC retention time 4.16 min.

EXAMPLE 1

Process C

[4-(4,9-Dimethoxy-1-oxo-1,3-dihydro-2H-benzo[f]isoindol-2-yl)phenyl]acetic acid

To a solution of ethyl 1,4-dimethoxy-2-methylnaphthalene-3-carboxylate (73 mg, 0.266 mmol) in carbon tetrachloride (10 ml) was added N-bromosuccinimide (47 mg, 0.266 mmol) and dibenzylperoxide (5 mg). The mixture was heated at reflux under nitrogen for 45 min, illuminating with a 200 W lamp. The reaction was cooled to room temperature, 4-aminophenyl acetic acid (40 mg, 0.266 mmol), triethylamine (74 μl, 0.53 mmol) and DMF (5 ml) added and the reaction stirred for 48 h. Acetic acid (glacial, 1 ml) was added to the reaction and the mixture refluxed for 3 h under nitrogen. Sodium metabisulphite solution (1 ml) was added and the reaction evaporated to dryness under vacuum. The product was partially purified by SPE (NH2, 10 g) eluting with methanol then 5% acetic acid in methanol. The fractions containing product were passed through a silica plug washing with 5% acetic acid in methanol. After evaporation of the solvents under vacuum, the residue was columned on a silica gel flash column eluting with a gradient (1:1 ethyl acetate/cyclohexane to 5% methanol, 1% acetic acid in 1:1 ethyl acetate/cyclohexane) to give [4-(4,9-dimethoxy-1-oxo-1,3-dihydro-2H-benzo[f]isoindol-2-yl)phenyl]acetic acid (15 mg, 15%).

δH $CDCl_3$ 8.40, (1H, d), 8.17, (1H, d), 7.90. (2H, d), 7.65, (1H, t), 7.59, (1H, t), 7.38, (2H, d), 5.02, (2H, s), 4.27, (3H, s), 4.08, (3H, s), 3.69, (2H, s). MS 378, [MH$^+$]. LC retention time 3.28 min.

EXAMPLE 2

Step 1 (Process E)

Ethyl[4-(4,9-diethoxy-1,3-dihydro-2H-benzo[f]isoindol-2-yl)phenyl]acetate

A solution of 2,3-bis(bromomethyl)-1,4-diethoxy-naphthalene (41 mg, 0.1 mmol) and 4-aminophenylacetic acid ethyl ester (20 mg, 0.11 mmol) in N,N-dimethylformamide (1 ml) was heated at 60° C. under nitrogen for 14 h. The solvent was removed in vacuo and the residue taken up in ethyl acetate (10 ml) and washed with 8% aqueous sodium bicarbonate solution (5 ml). The organic layer was dried over magnesium sulphate and the solvent removed in vacuo. Purification by flash column chromatography on silica gel eluting with 90% cyclohexane/ethyl acetate gave the product as a white solid (15 mg, 36%).

δH $CDCl_3$ 8.12 (2H, dd, J=6.5, 3.2), 7.50 (2H, dd, J=6.5, 3.2), 7.23 (2H, d, J=8.5), 6.73 (2H, d, J=8.5), 4.80 (4H, s), 4.17 (6H, m), 3.55 (2H, s), 1.56 (6H, m), 1.24 (3H, m); LC retention time 4.25 min, ms 420, [MH$^+$].

EXAMPLE 2

Step 2

[4-(4,9-diethoxy-1,3-dihydro-2H-benzo[f]isoindol-2-yl)phenyl]acetic acid

A solution of ethyl[4-(4,9-diethoxy-1,3-dihydro-2H-benzo[f]isoindol-2-yl)phenyl]acetate (10 mg, 0.024 mmol) in tetrahydrofuran (4 ml) and a solution of lithium hydroxide (6 mg, 0.24 mmol) in water (1 ml) were stirred vigorously for 14 h. The reaction mixture was diluted with water (10 ml) and extracted with ethyl acetate (2×5 ml) and the organic extracts discarded. The aqueous phase was acidified with 2N hydrochloric acid to pH=5 and extracted with ethyl acetate (3×5 ml). The combined organic extracts were dried over magnesium sulphate and the solvent removed in vacuo to give the product as a red solid (4 mg, 43%). δH $CDCl_3$ 8.13 (2H, dd, J=6.5, 3.2), 7.49, (2H, dd, J=6.5, 3.2), 7.24 (2H, d, 8.3), 6.75 (2H, d, J=8.3), 4.81 (4H, s), 4.19 (4H, q, J=7.0), 3.69 (2H, s), 1.53 (6H, t, J=7.0); LC retention time 3.92 min, ms 392, [MH$^+$].

General Methodology

Method A

A mixture of ethyl 1,4-dihydroxy-2,3-naphthalenedicarboxylate (1.0 g, 3.29 mmol), potassium carbonate (5 g, 36.2 mmol) and the alkyl halide (3.25 mmol) in acetone (20 ml) was heated at reflux under nitrogen for 8 h. The cooled reaction was filtered and the residue washed with acetone and ethyl acetate. The combined filtrate and washings were evaporated to dryness under vacuum. The residue was partitioned between hydrochloric acid (2N) and dichloromethane. The dichloromethane extract was evaporated to dryness under vacuum. The product was isolated by chromatography on a silica gel flash column eluting with an ethyl acetate/cyclohexane gradient (0-10% ethyl acetate).

Method B

A mixture of monoalkylated material (170 mg, 0.49 mmol), potassium carbonate (850 mg, 6.15 mmol) and the alkyl halide (1.0 mmol) in acetone (5 ml) was heated at reflux under nitrogen for 4 h. The cooled reaction was filtered and the residue washed with acetone and ethyl acetate. The combined filtrate and washings were evaporated to dryness under vacuum and the residue purified by SPE (silica) eluting with an ethyl acetate/cyclohexane gradient.

Method C

A mixture of ethyl 1,4-dihydroxy-2,3-naphthalenedicarboxylate (2 g, 6.57 mmol), potassium carbonate (10 g, 72.4 mmol) and the alkyl halide (64.1 mmol) in acetone (40 ml) was heated at reflux under nitrogen for 4 h. The cooled reaction was filtered and the residue washed with acetone and ethyl acetate. The combined filtrate and washings were evaporated to dryness under vacuum and the residue purified by SPE (silica) eluting with an ethyl acetate/cyclohexane gradient.

Method D

A mixture of the diester (13.87 mmol) and sodium hydroxide solution (2N, 25 ml) in ethanol (25 ml) was heated at reflux for 4 h. The resulting solution was acidified to pH1 with hydrochloric acid (2N) and extracted with ethyl acetate (×2). The extracts were dried (MgSO$_4$) and the solvent evaporated under vacuum.

Method E (Process A)

A mixture of diacid (0.57 mmol) and 4-aminophenylacetic acid (1.32 mmol) in glacial acetic acid (5 ml) was heated under reflux for 24 h. The cooled reaction was diluted with water, the precipitate formed filtered off and washed with water.

Method F

A mixture of diacid (0.56 mmol) and ethyl 4-aminophenylacetate (1.11 mmol) in glacial acetic acid (5 ml) was heated at reflux for 24 h. The cooled reaction was diluted with water, the precipitate formed filtered off and washed with water.

Method G (Process B—Step 1)

The phthalimide ester (0.32 mmol) was dissolved in glacial acetic acid (4 ml) and zinc powder (100 mesh, 300 mg, 4.59 mmol) added. The reaction was heated at reflux under nitrogen for 72 h. The hot reaction was filtered and the residue washed with hot acetic acid. The combined filtrate and washings were evaporated to dryness under vacuum. Methylamine (33% in ethanol, 2 ml) was added to the resulting solid and the suspension was stirred at room temperature for 20 min. The methylamine solution was evaporated under vacuum and the residue purified by SPE (silica) eluting with an ethyl acetate/cyclohexane gradient to give a mixture of isomeric γ-lactams.

Method H (Processes B and D—Step 2)

The γ-lactams (0.06 mmol) were mixed with potassium carbonate (1.09 mmol) in ethanol (2 ml) and water (1 ml) and heated at reflux for 4 h. The cooled solution was acidified to pH1 with hydrochloric acid (2M), the precipitate filtered off and washed with water. Dried at 40° C. under vacuum.

The following compounds were prepared using the above general methodologies:

Intermediate 9

Ethyl[4-(4,9-di-isopropoxy-1,3-dioxo-1,3-dihydro-2H-benzo[f]isoindol-2-yl)phenyl]acetate Ethyl[4-(4,9-di-isopropoxy-1,3-dioxo-1,3-dihydro-2H-benzo[f]isoindol-2-yl)phenyl]acetate was prepared in 49% yield from 1,4-di-isopropoxynaphthalene-2,3-dicarboxylic acid using method F.

δH [$^2$H$_6$]-DMSO 8.41, (2H, m), 7.83, (2H, m), 7.42, (4H, s), 5.02, (2H, m), 4.12, (2H, q), 3.76, (2H, s), 1.36, (12H, d), 1.22, (3H, t).

Intermediate 10

Ethyl[4-(4,9-dipropoxy-1,3-dioxo-1,3-dihydro-2H-benzo[f]isoindol-2-yl)phenyl]acetate Ethyl[4-(4,9-dipropoxy-1,3-dioxo-1,3-dihydro-2H-benzo[f]isoindol-2-yl)phenyl]acetate was prepared in 68% yield from 1,4-dipropoxynaphthalene-2,3-dicarboxylic acid using method F.

δH [$^2$H$_6$]-DMSO 8.35, (2H, m), 7.82, (2H, m), 7.37, (4H, s), 4.34, (4H, t), 4.07, (2H, q), 3.71, (2H, s), 1.83, (4H, m), 1.17, (3H, t), 1.01, (6H, t).

Intermediate 11

Ethyl[4-(4,9-dibutoxy-1,3-dioxo-1,3-dihydro-2H-benzo[f]isoindol-2-yl)phenyl]acetate Ethyl[4-(4,9-dibutoxy-1,3-dioxo-1,3-dihydro-2H-benzo[f]isoindol-2-yl)phenyl]acetate was prepared in 39% yield from 1,4-dibutoxynaphthalene-2,3-dicarboxylic acid using method F.

δH [$^2$H$_6$]-DMSO 8.39, (2H, m), 7.87, (2H, m), 7.42, (4H, s), 4.43, (4H, t), 4.12, (2H, q), 3.76, (2H, s), 1.85, (4H, m), 1.53, (4H, m), 1.22, (3H, t), 0.97, (6H, t).

Intermediate 12

Ethyl[4-(4,9-dihexyloxy-1,3-dioxo-1,3-dihydro-2H-benzo[f]isoindol-2-yl)phenyl]acetate Ethyl[4-(4,9-dihexyloxy-1,3-dioxo-1,3-dihydro-2H-benzo[f]isoindol-2-yl)phenyl]acetate was prepared from 1,4-dihexyloxynaphthalene-2,3-dicarboxylic acid using method F.

δH [$^2$H$_6$]-DMSO 8.38, (2H, m), 7.86, (2H, m), 7.42, (4H, s), 4.41, (4H, t), 4.12, (2H, q), 3.76, (2H, s), 1.85, (4H, m), 1.49, (4H, m), 1.32, (8H, m), 1.21, (3H, t), 0.87, (6H, t).

Intermediate 13

Ethyl[4-(4-ethoxy-9-isopropoxy-1,3-dioxo-1,3-dihydro-2H-benzo[f]isoindol-2-yl)phenyl]acetate Ethyl[4-(4-ethoxy-9-isopropoxy-1,3-dioxo-1,3-dihydro-2H-benzo[f]isoindol-2-yl)phenyl]acetate was prepared from 1-ethoxy-4-isopropoxynaphthalene-2,3-dicarboxylic acid using method F.

δH [$^2$H$_6$]-DMSO 8.36, (2H, m), 7.79, (2H, m), 7.37, (4H, s), 4.98, (1H, m), 4.42, (2H, q), 4.07, (2H, q), 3.71, (2H, s), 1.40, (3H, t), 1.31, (6H, d), 1.17, (3H, t).

Intermediate 14

Ethyl[4-(9-isopropoxy-4-propoxy-1,3-dioxo-1,3-dihydro-2H-benzo[f]isoindol-2-yl)phenyl]acetate Ethyl[4-(9-isopropoxy-4-propoxy-1,3-dioxo-1,3-dihydro-2H-benzo[f]isoindol-2-yl)phenyl]acetate was prepared from 4-isopropoxy-1-propoxynaphthalene-2,3-dicarboxylic acid using method F.

δH [²H₆]-DMSO 8.35, (2H, m), 7.80, (2H, m), 7.37, (4H, s), 4.97, (1H, m), 4.34, (2H, t), 4.07, (2H, q), 3.71, (2H, s), 1.83, (2H, m), 1.31, (6H, d), 1.71, (3H, t), 1.01, (3H, t).

Intermediate 15

Ethyl[4-(4-hexyloxy-9-isopropoxy-1,3-dioxo-1,3-dihydro-2H-benzo[f]isoindol-2-yl)phenyl]acetate Ethyl[4-(4-hexyloxy-9-isopropoxy-1,3-dioxo-1,3-dihydro-2H-benzo[f]isoindol-2-yl)phenyl]acetate was prepared from 1-hexyloxy-4-isopropoxynaphthalene-2,3-dicarboxylic acid using method F.

δH [²H₆]-DMSO 8.37, (1H, m), 8.32, (1H, m), 7.80, (2H, m), 7.37, (4H, s), 4.97, (1H, m), 4.37, (2H, t), 4.07, (2H, q), 3.71, (2H, s), 1.81, (2H, m), 1.45, (2H, m), 1.35-1.26, (10H, m), 1.17, (3H, t), 0.82, (3H, t).

Intermediate 16

1,4-Di-isopropoxynaphthalene-2,3-dicarboxylic acid 1,4-Di-isopropoxynaphthalene-2,3-dicarboxylic acid was prepared from ethyl 1,4-di-propoxynaphthalene-2,3-dicarboxylate using method D.

δH [²H₆]-DMSO 8.16, (2H, m), 7.67, (2H, m), 4.43, (2H, m), 1.26, (12H, d).

Intermediate 17

1,4-Dipropoxynaphthalene-2,3-dicarboxylic acid 1,4-Dipropoxynaphthalene-2,3-dicarboxylic acid was prepared from ethyl 1,4-dipropoxynaphthalene-2,3-dicarboxylate using method D.

δH [²H₆]-DMSO 8.14, (2H, m), 7.71, (2H, m), 4.01, (4H, t), 1.83, (4H, m), 1.05, (6H, t).

Intermediate 18

1,4-Dibutoxynaphthalene-2,3-dicarboxylic acid 1,4-Dibutoxynaphthalene-2,3-dicarboxylic acid was prepared from ethyl 1,4-dibutoxynaphthalene-2,3-dicarboxylate using method D.

δH [²H₆]-DMSO 8.12, (2H, m), 7.12, (2H, m), 4.05, (4H, t), 1.80, (4H, m), 1.52, (4H, m), 0.97, (6H, t).

Intermediate 19

1,4-Dihexyloxynaphthalene-2,3-dicarboxylic acid 1,4-Dihexyloxynaphthalene-2,3-dicarboxylic acid was prepared from ethyl 1,4-dihexyloxynaphthalene-2,3-dicarboxylate using method D.

δH [²H₆]-DMSO 8.39, (2H, m), 7.92, (2H, m), 4.46, (4H, t), 1.85, (4H, m), 1.49, (4H, m), 1.32, (8H, m), 0.88, (6H, t).

Intermediate 20

1-Ethoxy-4-isopropoxynaphthalene-2,3-dicarboxylic acid

1-Ethoxy-4-isopropoxynaphthalene-2,3-dicarboxylic acid was prepared from ethyl 1-ethoxy-4-isopropoxynaphthalene-2,3-dicarboxylate using method D.

δH [²H₆]-DMSO 8.18, (1H, m), 8.12, (1H, m), 7.69, (2H, m), 4.40, (1H, m), 4.11, (2H, q), 1.41, (3H, t), 1.27, (6H, d).

Intermediate 21

4-Isopropoxy-1-propoxynaphthalene-2,3-dicarboxylic acid

4-Isopropoxy-1-propoxynaphthalene-2,3-dicarboxylic acid was prepared from ethyl 4-isopropoxy-1-propoxynaphthalene-2,3-dicarboxylate using method D.

δH [²H₆]-DMSO 8.18, (1H, m), 8.11, (1H, m), 7.70, (2H, m), 4.41, (1H, m), 4.02, (2H, t), 1.83, (2H, m), 1.27, (6H, d), 1.06, (3H, t).

Intermediate 22

1-Butoxy-4-isopropoxynaphthalene-2,3-dicarboxylic acid

1-Butoxy-4-isopropoxynaphthalene-2,3-dicarboxylic acid was prepared from ethyl 1-butoxy-4-isopropoxynaphthalene-2,3-dicarboxylate using method D.

δH [²H₆]-DMSO 8.18, (1H, m), 8.09, (1H, m), 7.69, (2H, m), 4.40, (1H, m), 4.05, (2H, t), 1.80, (2H, m), 1.52, (2H, m), 1.26, (6H, d), 0.97, (3H, t).

Intermediate 23

1-Hexyloxy-4-isopropoxynaphthalene-2,3-dicarboxylic acid

1-Hexyloxy-4-isopropoxynaphthalene-2,3-dicarboxylic acid was prepared from ethyl 1-hexyloxy-4-isopropoxynaphthalene-2,3-dicarboxylate using method D.

δH [²H₆]-DMSO 8.18, (1H, m), 8.09, (1H, m), 7.70, (2H, m), 4.40, (1H, m), 4.04, (2H, t), 1.81, (2H, m), 1.49, (2H, m), 1.34, (4H, m), 1.27, (6H, d), 0.90, (3H, t).

Intermediate 24

Ethyl 1,4-di-isopropoxynaphthalene-2,3-dicarboxylate

Ethyl 1,4-di-isopropoxynaphthalene-2,3-dicarboxylate was prepared from ethyl 1,4-dihydroxynaphthalene-2,3-dicarboxylate and 2-iodopropane using method C.

δH [²H₆]-DMSO 8.18, (2H, m), 7.73, (2H, m), 4.37, (2H, m), 4.28, (4H, q), 1.30, (6H, t), 1.25, (12H, d).

Intermediate 25

Ethyl 1,4-dipropoxynaphthalene-2,3-dicarboxylate

Ethyl 1,4-dipropoxynaphthalene-2,3-dicarboxylate was prepared from ethyl 1,4-dihydroxynaphthalene-2,3-dicarboxylate and 1-iodopropane using method C.

δH [²H₆]-DMSO 8.16, (2H, m), 7.77, (2H, m), 4.29, (4H, q), 4.00, (4H, t), 1.83, (4H, m), 1.30, (4H, t), 1.04, (4H, t).

Intermediate 26

Ethyl 1,4-dibutoxynaphthalene-2,3-dicarboxylate

Ethyl 1,4-dibutoxynaphthalene-2,3-dicarboxylate was prepared from ethyl 1,4-dihydroxynaphthalene-2,3-dicarboxylate and 1-iodobutane using method C.

δH [²H₆]-DMSO 8.15, (2H, m), 7.76, (2H, m), 4.29, (4H, q), 4.03, (4H, t), 1.79, (4H, m), 1.50, (4H, m), 1.30, (6H, t), 0.96, (6H, t).

Intermediate 27

Ethyl 1,4-dihexyloxynaphthalene-2,3-dicarboxylate

Ethyl 1,4-dihexyloxynaphthalene-2,3-dicarboxylate was prepared from ethyl 1,4-dihydroxynaphthalene-2,3-dicarboxylate and 2-iodohexane using method C.

δH [²H₆]-DMSO 8.14, (2H, m), 7.76, (2H, m), 4.29, (4H, q), 4.03, (4H, t), 1.81, (4H, m), 1.47, (4H, m), 1.38-1.21, (14H, m), 0.88, (6H, t).

Intermediate 28

Ethyl 1-ethoxy-4-isopropoxynaphthalene-2,3-dicarboxylate

Ethyl 1-ethoxy-4-isopropoxynaphthalene-2,3-dicarboxylate was prepared in 91% yield from ethyl 1-hydroxy-4-isopropoxynaphthalene-2,3-dicarboxylate and iodoethane using method B.

δH CDCl₃ 8.22, (1H, m), 8.13, (1H, m), 7.59, (2H, m), 4.40, (5H, m), 4.18, (2H, q), 1.49, (3H, t), 1.43-1.38, (6H, m), 1.34, (6H, d).

Intermediate 29

Ethyl 4-isopropoxy-1-propoxynaphthalene-2,3-dicarboxylate

Ethyl 4-isopropoxy-1-propoxynaphthalene-2,3-dicarboxylate was prepared in 91% yield from ethyl 1-hydroxy-4-isopropoxynaphthalene-2,3-dicarboxylate and 1-iodopropane using method B.

δH CDCl₃ 8.22, (1H, m), 8.14, (1H, m), 7.60, (2H, m), 4.40, (5H, m), 4.07, (2H, t), 1.92, (2H, m), 1.40, (6H, m), 1.34, (6H, d), 1.10, (3H, t).

Intermediate 30

Ethyl 1-butoxy-4-isopropoxynaphthalene-2,3-dicarboxylate

Ethyl 1-butoxy-4-isopropoxynaphthalene-2,3-dicarboxylate was prepared from ethyl 1-hydroxy-4-isopropoxynaphthalene-2,3-dicarboxylate and 1-iodobutane using method B.

δH [²H₆]-DMSO 8.20, (1H, m), 8.12, (1H, m), 7.75, (2H, m), 4.38-4.25, (5H, m), 4.04, (2H, t), 1.80, (2H, m), 1.50, (2H, m), 1.30, (6H, t), 1.25, (6H, d), 0.96, (3H, t).

Intermediate 31

Ethyl 1-hexyloxy-4-isopropoxynaphthalene-2,3-dicarboxylate

Ethyl 1-hexyloxy-4-isopropoxynaphthalene-2,3-dicarboxylate was prepared in 80 yield from ethyl 1-hydroxy-4-isopropoxynaphthalene-2,3-dicarboxylate and 1-iodohexane using method B.

δH CDCl₃ 8.21, (1H, m), 8.13, (1H, m), 7.59, (2H, m), 4.40, (5H, m), 4.10, (2H, t), 1.90, (2H, m), 1.53, (2H, m), 1.45-1.31, (16H, m), 0.92, (3H, t).

Intermediate 32

Ethyl 1-ethoxy-4-hydroxynaphthalene-2,3-dicarboxylate

Ethyl 1-ethoxy-4-hydroxynaphthalene-2,3-dicarboxylate was prepared from ethyl 1,4-dihydroxynaphthalene-2,3-dicarboxylate and iodoethane using method A.

δH [²H₆]-DMSO 8.36, (1H, d), 8.06, (1H, d), 7.83, (1H, m), 7.72, (1H, m), 4.35, (4H, m), 4.03, (2H, q), 1.39, (3H, t), 1.32, (6H, m).

Intermediate 33

Ethyl 1-hydroxy-4-isopropoxynaphthalene-2,3-dicarboxylate

Ethyl 1-hydroxy-4-isopropoxynaphthalene-2,3-dicarboxylate was prepared in 36% yield from ethyl 1,4-dihydroxynaphthalene-2,3-dicarboxylate and 2-iodopropane using method A.

δH CDCl₃ 12.3, (1H, s), 8.45, (1H, d), 8.10, (1H, d), 7.65, (1H, m), 7.55, (1H, m), 4.42, (1H, m), 1.41, (6H, t), 1.32, (6H, d).

EXAMPLE 4

Step 1 (Process B)

Ethyl[4-(4,9-di-isopropoxy-1-oxo-1,3-dihydro-2H-benzo[f]isoindol-2-yl)phenyl]acetate Ethyl[4-(4,9-di-isopropoxy-1-oxo-1,3-dihydro-2H-benzo[f]isoindol-2-yl)phenyl]acetate was prepared in 16% yield from ethyl[4-(4,9-di-isopropoxy-1,3-dioxo-1,3-dihydro-2H-benzo[f]isoindol-2-yl)phenyl]acetate using method G.

δH [²H₆]-DMSO 8.34, (1H, d), 8.16, (1H, d), 7.93, (2H, d), 7.68, (1H, t), 7.60, (1H, t), 7.34, (2H, d), 5.10, (2H, s), 5.01, (1H, m), 4.68, (1H, m), 4.10, (2H, q), 3.69, (2H, s), 1.40, (3H, d), 1.35, (3H, d), 1.19, (3H, t).

EXAMPLE 4

Step 2

[4-(4,9-Di-isopropoxy-1-oxo-1,3-dihydro-2H-benzo[f]isoindol-2-yl)phenyl]acetic acid

[4-(4,9-Di-isopropoxy-1-oxo-1,3-dihydro-2H-benzo[f]isoindol-2-yl)phenyl]acetic acid was prepared in 81% yield from ethyl[4-(4,9-di-isopropoxy-1-oxo-1,3-dihydro-2H-benzo[f]isoindol-2-yl)phenyl]acetate using method H.

δH [²H₆]-DMSO 8.34, (1H, d), 8.17, (1H, d), 7.91, (2H, d), 7.69, (1H, m), 7.61, (1H, m), 7.34, (2H, d), 5.10, (2H, s), 5.02, (1H, m), 4.68, (1H, m), 3.59, (2H, s), 1.38, (6H, d), 1.34, (6H, d). MS 434, [MH⁺]. LC retention time 3.91 min.

EXAMPLE 5

Step 1 (Process B)

Ethyl[4-(4,9-dipropoxy-1-oxo-1,3-dihydro-2H-benzo[f]isoindol-2-yl)phenyl]acetate Ethyl[4-(4,9-dipropoxy-1-oxo-1,3-dihydro-2H-benzo[f]isoindol-2-yl)phenyl]acetate was prepared in 13% yield from ethyl[4-(4,9-dipropoxy-1,3-dioxo-1,3-dihydro-2H-benzo[f]
isoindol-2-yl)phenyl]acetate using method G.

δH [$^2$H$_6$]-DMSO 8.32, (1H, d), 8.19, (1H, d), 7.93, (2H, d),
7.72, (1H, t), 7.65, (1H, t), 7.36, (2H, d), 5.19, (2H, s), 4.30,
(2H, t), 4.22, (2H, t), 4.10, (2H, q), 3.69, (2H, s), 1.87, (4H,
m), 1.20, (3H, t), 1.13-1.05, (6H, m).

EXAMPLE 5

Step 2

[4-(4,9-Dipropoxy-1-oxo-1,3-dihydro-2H-benzo[f]
isoindol-2-yl)phenyl]acetic acid

[4-(4,9-Dipropoxy-1-oxo-1,3-dihydro-2H-benzo[f]isoindol-2-yl)phenyl]acetic acid was prepared in 89% yield from
ethyl[4-(4,9-dipropoxy-1-oxo-1,3-dihydro-2H-benzo[f]
isoindol-2-yl)phenyl]acetate using method H.

δH [$^2$H$_6$]-DMSO 8.32, (1H, d), 8.19, (1H, d), 7.91, (2H, d),
7.71, (1H, t), 7.65, (1H, t), 7.65, (2H, d), 5.19, (2H, s), 4.30,
(2H, t), 4.22, (2H, t), 3.59, (2H, s), 1.89, (4H, m), 1.09, (6H,
m). MS 434, [MH$^+$]. LC retention time 3.97 min.

EXAMPLE 6

Step 1 (Process B)

Ethyl[4-(4,9-dibutoxy-1-oxo-1,3-dihydro-2H-benzo
[f]isoindol-2-yl)phenyl]acetate Ethyl[4-(4,9-dibutoxy-1-oxo-1,3-dihydro-2H-benzo[f]
isoindol-2-yl)phenyl]acetate was prepared in 26% yield from
ethyl[4-(4,9-dibutoxy-1,3-dioxo-1,3-dihydro-2H-benzo[f]
isoindol-2-yl)phenyl]acetate using method G.

δH [$^2$H$_6$]-DMSO 8.22, (1H, d), 8.09, (1H, d), 7.84, (2H, d),
7.63, (1H, t), 7.57, (1H, t), 7.27, (2H, d), 5.10, (2H, s), 4.26,
(2H, t), 4.17, (2H, t), 4.02, (2H, q), 3.60, (2H, s), 1.77, (4H,
quintet), 1.49, (4H, m), 1.12, (3H, t), 0.91, (6H, q).

EXAMPLE 6

Step 2

[4-(4,9-Dibutoxy-1-oxo-1,3-dihydro-2H-benzo[f]
isoindol-2-yl)phenyl]acetic acid

[4-(4,9-Dibutoxy-1-oxo-1,3-dihydro-2H-benzo[f]isoindol-2-yl)phenyl]acetic acid was prepared in 98% yield from
ethyl[4-(4,9-dibutoxy-1-oxo-1,3-dihydro-2H-benzo[f]isoindol-2-yl)phenyl]acetate using method H.

δH [$^2$H$_6$]-DMSO 8.30, (1H, d), 8.18, (1H, d), 7.91, (2H, d),
7.71, (1H, t), 7.65, (1H, t), 7.35, (2H, d), 5.19, (2H, s), 4.34,
(2H, t), 4.26, (2H, t), 3.59, (2H, s), 1.85, (4H, m), 1.57, (4H,
m), 0.99, (6H, m). MS 462, [MH$^+$]. LC retention time 4.25
min.

EXAMPLE 7

Step 1 (Process B)

Ethyl[4-(4,9-dihexyloxy-1-oxo-1,3-dihydro-2H-
benzo[f]isoindol-2-yl)phenyl]acetate Ethyl[4-(4,9-dihexyloxy-1-oxo-1,3-dihydro-2H-benzo[f]
isoindol-2-yl)phenyl]acetate was prepared in 28% yield from
ethyl[4-(4,9-dihexyloxy-1,3-dioxo-1,3-dihydro-2H-benzo
[f]isoindol-2-yl)phenyl]acetate using method G.

δH [$^2$H$_6$]-DMSO 8.19, (1H, d), 8.07, (1H, d), 7.82, (2H, d),
7.60, (1H, t), 7.54, (1H, t), 7.25, (2H, d), 5.08, (2H, s), 4.23,
(2H, t), 4.15, (2H, t), 3.99, (2H, q), 3.58, (2H, s), 1.75, (4H,
quintet), 1.50-1.36, (4H, m), 1.29-1.21, (8H, m), 1.09, (3H, t),
0.79, (6H, q).

EXAMPLE 7

Step 2

[4-(4,9-Dihexyloxy-1-oxo-1,3-dihydro-2H-benzo[f]
isoindol-2-yl)phenyl]acetic acid

[4-(4,9-Dihexyloxy-1-oxo-1,3-dihydro-2H-benzo[f]
isoindol-2-yl)phenyl]acetic acid was prepared in 97% yield
from ethyl[4-(4,9-dihexyloxy-1-oxo-1,3-dihydro-2H-benzo
[f]isoindol-2-yl)phenyl]acetate using method H.

δH [$^2$H$_6$]-DMSO 8.30, (1H, d), 8.17, (1H, d), 7.91, (2H, d),
7.71, (1H, t), 7.64, (1H, t), 7.34, (2H, d), 5.18, (2H, s), 4.33,
(2H, t), 4.25, (2H, t), 3.59, (2H, s), 1.86, (4H, m), 1.54, (4H,
m), 1.35, (8H, m), 0.90, (6H, m). MS 518, [MH$^+$]. LC retention time 4.76 min.

EXAMPLE 8

Step 1 (Process B)

Ethyl[4-(4-ethoxy-9-isopropoxy-1-oxo-1,3-dihydro-
2H-benzo[f]isoindol-2-yl)phenyl]acetate and ethyl
[4-(9-ethoxy-4-isopropoxy-1-oxo-1,3-dihydro-2H-
benzo[f]isoindol-2-yl)phenyl]acetate A mixture of ethyl[4-(4-ethoxy-9-isopropoxy-1-oxo-1,3-
dihydro-2H-benzo[f]isoindol-2-yl)phenyl]acetate and ethyl
[4-(9-ethoxy-4-isopropoxy-1-oxo-1,3-dihydro-2H-benzo[f]
isoindol-2-yl)phenyl]acetate (60:40) was prepared in 20%
yield from ethyl[4-(4-ethoxy-9-isopropoxy-1,3-dioxo-1,3-
dihydro-2H-benzo[f]isoindol-2-yl)phenyl]acetate using
method G.

δH [$^2$H$_6$]-DMSO 8.25, (1H, m), 8.09, (1H, m), 7.85, (2H,
d), 7.64-7.58, (2H, m), 7.26, (2H, d), 5.09, (1.2H, s), 5.02,
(0.8H, s), 4.90, (0.6H, m), 4.60, (0.4H, m), 4.32, (0.8H, q),
4.22, (1.2H, q), 4.01, (2H, q), 3.60, (2H, s), 1.38, (3H, m),
1.29, (2.4H, d), 1.24, (3.6H, d), 1.11, (3H, t).

EXAMPLE 8

Step 2

[4-(4-Ethoxy-9-isopropoxy-1-oxo-1,3-dihydro-2H-
benzo[f]isoindol-2-yl)phenyl]acetic acid and [4-(9-
ethoxy-4-isopropoxy-1-oxo-1,3-dihydro-2H-benzo
[f]isoindol-2-yl)phenyl]acetic acid A mixture of [4-(4-ethoxy-9-isopropoxy-1-oxo-1,3-dihydro-2H-benzo[f]isoindol-2-yl)phenyl]acetic acid and [4-(9-
ethoxy-4-isopropoxy-1-oxo-1,3-dihydro-2H-benzo[f]isoindol-2-yl)phenyl]acetic acid (60:40) was prepared in 98%
yield from ethyl[4-(4-ethoxy-9-isopropoxy-1-oxo-1,3-dihydro-2H-benzo[f]isoindol-2-yl)phenyl]acetate and ethyl[4-(9-
ethoxy-4-isopropoxy-1-oxo-1,3-dihydro-2H-benzo[f]isoindol-2-yl)phenyl]acetate (60:40) using method H.

δH [$^2$H$_6$]-DMSO 8.34, (1H, m), 8.18, (1H, m), 7.92, (2H,
d), 7.70, (1H, t), 7.68, (1H, t), 7.34, (2H, d), 5.18, (1.2H, s),
5.11, (0.8H, s), 5.01, (0.6H, m), 4.69, (0.4H, m), 4.40, (0.8H,
q), 4.31, (1.2H, q), 3.59, (2H, s), 1.46, (3H, m), 1.37, (2.4H,
d), 1.33, (3.6H, d). MS 420, [MH$^+$]. LC retention time 3.73
min.

EXAMPLE 9

Step 1 (Process B)

Ethyl[4-(9-isopropoxy-4-propoxy-1-oxo-1,3-dihydro-2H-benzo[f]isoindol-2-yl)phenyl]acetate and ethyl[4-(4-isopropoxy-9-propoxy-1-oxo-1,3-dihydro-2H-benzo[f]isoindol-2-yl)phenyl]acetate A mixture of ethyl[4-(9-isopropoxy-4-propoxy-1,3-dihydro-2H-benzo[f]isoindol-2-yl)phenyl]acetate and ethyl[4-(4-isopropoxy-9-propoxy-1-oxo-1,3-dihydro-2H-benzo[f]isoindol-2-yl)phenyl]acetate (60:40) was prepared in 21% yield from ethyl[4-(9-isopropoxy-4-propoxy-1,3-dioxo-1,3-dihydro-2H-benzo[f]isoindol-2-yl)phenyl]acetate using method G.

δH [$^2$H$_6$]-DMSO 8.25, (1H, m), 8.10, (1H, m), 7.85, (2H, m), 7.62, (1H, m), 7.53, (1H, m), 7.27, (2H, d), 5.10, (1.2H, s), 5.02, (0.8H, s), 4.91, (0.6H, m), 4.58, (0.4H, m), 4.23, (0.8H, t), 4.13, (1.2H, t), 4.01, (2H, q), 3.60, (2H, s), 1.80, (2H, m), 1.29, (2.4H, d), 1.24, (3.6H, d), 1.11, (3H, t), 1.01, (3H, m).

EXAMPLE 9

Step 2

[4-(9-isopropoxy-4-propoxy-1-oxo-1,3-dihydro-2H-benzo[f]isoindol-2-yl)phenyl]acetic acid and [4-(4-isopropoxy-9-propoxy-1-oxo-1,3-dihydro-2H-benzo[f]isoindol-2-yl)phenyl]acetic acid A mixture of [4-(9-isopropoxy-4-propoxy-1-oxo-1,3-dihydro-2H-benzo[f]isoindol-2-yl)phenyl]acetic acid and [4-(4-isopropoxy-9-propoxy-1-oxo-1,3-dihydro-2H-benzo[f]isoindol-2-yl)phenyl]acetic acid (60:40) was prepared in quantitative yield from ethyl[4-(9-isopropoxy-4-propoxy-1-oxo-1,3-dihydro-2H-benzo[f]isoindol-2-yl)phenyl]acetate and ethyl[4-(4-isopropoxy-9-propoxy-1-oxo-1,3-dihydro-2H-benzo[f]isoindol-2-yl)phenyl]acetate (60:40) using method H.

δH [$^2$H$_6$]-DMSO 8.34, (1H, m), 8.18, (1H, m), 7.92, (2H, m), 7.70. (1H, t), 7.63, (1H, m), 7.34, (2H, d), 5.18, (1.2H, s), 5.11, (0.8H, s), 5.01, (0.6H, m), 4.68, (0.4H, m), 4.32, (0.8H, q), 4.22, (1.2H, q), 3.59, (2H, s), 1.89, (2H, m), 1.37, (2.4H, d), 1.33, (3.6H, d), 1.10, (3H, m). MS 434, [MH$^+$]. LC retention time 3.89 min.

EXAMPLE 10

Step 1 (Process B)

Ethyl[4-(4-hexyloxy-9-isopropoxy-1-oxo-1,3-dihydro-2H-benzo[f]isoindol-2-yl)phenyl]acetate and ethyl[4-(9-hexyloxy-4-isopropoxy-1-oxo-1,3-dihydro-2H-benzo[f]isoindol-2-yl)phenyl]acetate A mixture of ethyl[4-(4-hexyloxy-9-isopropoxy-1-oxo-1,3-dihydro-2H-benzo[f]isoindol-2-yl)phenyl]acetate and ethyl[4-(9-hexyloxy-4-isopropoxy-1-oxo-1,3-dihydro-2H-benzo[f]isoindol-2-yl)phenyl]acetate (60:40) was prepared in 16% yield from ethyl[4-(4-hexyloxy-9-propoxy-1,3-dioxo-1,3-dihydro-2H-benzo[f]isoindol-2-yl)phenyl]acetate using method G.

δH [$^2$H$_6$]-DMSO 8.33, (1H, m), 8.17, (1H, m), 7.94, (2H, m), 7.70, (1H, m), 7.64, (1H, m), 7.35, (2H, d), 5.18, (1.2H, s), 5.11, (0.8H, s), 5.00, (0.6H, m), 4.69, (0.4H, m), 4.35, (0.8H, t), 4.25, (1.2H, t), 4.10, (2H, q), 3.69, (2H, s), 1.87, (2H, m), 1.60-1.45, (2H, m), 1.37, (2.4H, d), 1.33, (3.6H, d), 1.20, (3H, t), 0.91, (3H, m).

EXAMPLE 10

Step 2

[4-(4-Hexyloxy-9-isopropoxy-1-oxo-1,3-dihydro-2H-benzo[f]isoindol-2-yl)phenyl]acetic acid and [4-(9-hexyloxy-4-isopropoxy-1-oxo-1,3-dihydro-2H-benzo[f]isoindol-2-yl)phenyl]acetic acid A mixture of [4-(4-hexyloxy-9-isopropoxy-1-oxo-1,3-dihydro-2H-benzo[f]isoindol-2-yl)phenyl]acetic acid and [4-(9-hexyloxy-4-isopropoxy-1-oxo-1,3-dihydro-2H-benzo[f]isoindol-2-yl)phenyl]acetic acid (60:40) was prepared in 78% yield from ethyl[4-(4-hexyloxy-9-isopropoxy-1-oxo-1,3-dihydro-2H-benzo[f]isoindol-2-yl)phenyl]acetate and ethyl[4-(9-hexyloxy-4-isopropoxy-1-oxo-1,3-dihydro-2H-benzo[f]isoindol-2-yl)phenyl]acetate (60:40) using method H.

δH [$^2$H$_6$]-DMSO 8.35, (0.6H, d), 8.30, (0.4H, d), 8.17, (2H, m), 7.91, (2H, m), 7.70, (1H, t), 7.63, (1H, m), 7.34, (2H, d), 5.18, (1.2H, s), 5.10, (0.8H, s), 5.00, (0.6H, m), 4.68, (0.4H, m), 4.35, (0.8H, q), 4.25, (1.2H, q), 3.59, (2H, s), 1.87, (2H, m), 1.54, (2H, m), 1.35, (10H, m), 0.91, (3H, m). MS 476, [MH$^+$]. LC retention time 4.32 min.

EXAMPLE 11

Step 1 (Process D)

Ethyl[4-(4-methoxy-1-oxo-1,3-dihydro-2H-benzo[f]isoindol-2-yl)phenyl]acetate

3-Hydroxy-4-methoxynaphtho[2,3-c]furan-1(3H)-one (50 mg, 0.22 mmol) and ethyl 4-aminophenylacetate (47 mg, 0.26 mmol) in dichloromethane (5 ml) were stirred at room temperature under nitrogen for 1 hour. Sodium triacetoxyborohydride (138 mg, 0.66 mmol) was added and stirring continued for 24 h. The reaction was adjusted to pH14 with sodium hydroxide solution (2N) and extracted with dichloromethane (3×5 ml). The combined extracts were evaporated under vacuum and the residue triturated with cyclohexane/ether to give ethyl[4-(4-methoxy-1-oxo-1,3-dihydro-2H-benzo[f]isoindol-2-yl)phenyl]acetate as a white solid (45 mg, 54%).

δH [$^2$H$_6$]-DMSO 8.24, (1H, d), 8.16, (1H, d), 8.13, (1H, s), 7.99, (2H, d), 7.64, (2H, m), 7.37, (2H, d), 5.44, (2H, s), 4.26, (3H, s), 4.10, (2H, q), 3.69, (2H, s), 1.20, (3H, t).

EXAMPLE 11

Step 2

[4-(4-Methoxy-1-oxo-1,3-dihydro-2H-benzo[f]isoindol-2-yl)phenyl]acetic acid

[4-(4-Methoxy-1-oxo-1,3-dihydro-2H-benzo[f]isoindol-2-yl)phenyl]acetic acid was prepared in quantitative yield from ethyl[4-(4-methoxy-1-oxo-1,3-dihydro-2H-benzo[f]isoindol-2-yl)phenyl]acetate using method H.

δH [$^2$H$_6$]-DMSO 8.19, (1H, d), 8.09, (2H, m), 7.92, (2H, d), 7.59, (2H, m), 7.31, (2H, d), 5.39, (2H, s), 4.21, (3H, s), 3.56, (2H, s). MS 348, [MH$^+$]. LC retention time 3.50 min.

EXAMPLE 12

[4-(4,9-Diethoxy-1,3-dioxo-1,3-dihydro-2H-benzo[f]isoindol-2-yl)phenyl]acetic acid

[4-(4,9-Diethoxy-1,3-dioxo-1,3-dihydro-2H-benzo[f]isoindol-2-yl)phenyl]acetic acid was prepared from 1,4-diethoxynaphthalene-2,3-dicarboxylic acid using method E.

δH [$^2$H$_6$]-DMSO 8.35, (2H, m), 7.81, (2H, m), 7.36, (4H, s), 4.43, (4H, q), 3.62, (2H, s), 1.40, (6H, t). MS 420, [MH$^+$]. LC retention time 3.58 min.

EXAMPLE 13

[4-(4,9-Di-isopropoxy-1,3-dioxo-1,3-dihydro-2H-benzo[f]isoindol-2-yl)phenyl]acetic acid

[4-(4,9-Di-isopropoxy-1,3-dioxo-1,3-dihydro-2H-benzo[f]isoindol-2-yl)phenyl]acetic acid was prepared from 1,4-di-isopropoxynaphthalene-2,3-dicarboxylic acid using method E.

δH [$^2$H$_6$]-DMSO 8.41, (2H, m), 7.83, (2H, m), 7.41, (4H, s), 5.02, (2H, m), 3.66, (2H, s), 1.36, (12H, d). MS 448, [MH$^+$]. LC retention time 3.74 min.

EXAMPLE 14

[4-(4,9-Dipropoxy-1,3-dioxo-1,3-dihydro-2H-benzo[f]isoindol-2-yl)phenyl]acetic acid

[4-(4,9-Dipropoxy-1,3-dioxo-1,3-dihydro-2H-benzo[f]isoindol-2-yl)phenyl]acetic acid was prepared from 1,4-dipropoxynaphthalene-2,3-dicarboxylic acid using method E.

δH [$^2$H$_6$]-DMSO 8.39, (2H, m), 7.87, (2H, m), 7.41, (4H, s), 4.39, (4H, t), 3.67, (2H, s), 1.87, (4H, m), 1.05, (6H, t).). MS 448, [MH$^+$]. LC retention time 3.89 min.

EXAMPLE 15

[4-(4,9-Dibutoxy-1,3-dioxo-1,3-dihydro-2H-benzo[f]isoindol-2-yl)phenyl]acetic acid

[4-(4,9-Dibutoxy-1,3-dioxo-1,3-dihydro-2H-benzo[f]isoindol-2-yl)phenyl]acetic acid was prepared from 1,4-dibutoxynaphthalene-2,3-dicarboxylic acid using method E.

δH [$^2$H$_6$]-DMSO 8.39, (2H, m), 7.88, (2H, m), 7.41, (4H, s), 4.43, (4H, t), 3.67, (2H, s), 1.84, (4H, m), 1.52, (4H, m), 0.96, (6H, t). MS 476, [MH$^+$]. LC retention time 4.15 min.

EXAMPLE 16

[4-(4,9-Dihexyloxy-1,3-dioxo-1,3-dihydro-2H-benzo[f]isoindol-2-yl)phenyl]acetic acid

[4-(4,9-Dihexyloxy-1,3-dioxo-1,3-dihydro-2H-benzo[f]isoindol-2-yl)phenyl]acetic acid was prepared from 1,4-dihexyloxynaphthalene-2,3-dicarboxylic acid using method E.

δH [$^2$H$_6$]-DMSO 8.38, (2H, m), 7.86, (2H, m), 7.41, (4H, s), 4.42, (4H, t), 3.67, (2H, s), 1.85, (4H, m), 1.49, (4H, m), 1.32, (8H, m), 0.87, (6H, t).). MS 532, [MH$^+$]. LC retention time 4.62 min.

EXAMPLE 17

[4-(4-Ethoxy-9-isopropoxy-1,3-dioxo-1,3-dihydro-2H-benzo[f]isoindol-2-yl)phenyl]acetic acid

[4-(4-Ethoxy-9-isopropoxy-1,3-dioxo-1,3-dihydro-2H-benzo[f]isoindol-2-yl)phenyl]acetic acid was prepared from 1-ethoxy-4-isopropoxynaphthalene-2,3-dicarboxylic acid using method E.

δH [$^2$H$_6$]-DMSO 8.41, (2H, m), 7.84, (2H, m), 7.41, (4H, s), 5.03, (1H, m), 4.48, (2H, q), 3.67, (2H, s), 1.45, (3H, t), 1.36, (6H, d). MS 434, [MH$^+$]. LC retention time 3.66 min.

EXAMPLE 18

[4-(9-isopropoxy-4-propoxy-1,3-dioxo-1,3-dihydro-2H-benzo[f]isoindol-2-yl)phenyl]acetic acid

[4-(9-isopropoxy-4-propoxy-1,3-dioxo-1,3-dihydro-2H-benzo[f]isoindol-2-yl)phenyl]acetic acid was prepared from 4-isopropoxy-1-propoxynaphthalene-2,3-dicarboxylic acid using method E.

δH [$^2$H$_6$]-DMSO 8.41, (2H, m), 7.84, (2H, m), 7.41, (4H, s), 5.02, (1H, m), 4.39, (2H, t), 3.66, (2H, s), 1.88, (2H, m), 1.36, (6H, d), 1.05, (3H, t). MS 448, [MH$^+$]. LC retention time 3.81 min.

EXAMPLE 19

[4-(4-Butoxy-9-isopropoxy-1,3-dioxo-1,3-dihydro-2H-benzo[f]isoindol-2-yl)phenyl]acetic acid

[4-(4-Butoxy-9-isopropoxy-1,3-dioxo-1,3-dihydro-2H-benzo[f]isoindol-2-yl)phenyl]acetic acid was prepared from 1-butoxy-4-isopropoxynaphthalene-2,3-dicarboxylic acid using method E.

δH [$^2$H$_6$]-DMSO 8.42, (1H, m), 8.37, (1H, m), 7.85, (2H, m), 7.41, (4H, s), 5.02, (1H, m), 4.43, (2H, t), 3.66, (2H, s), 1.85, (2H, m), 1.53, (2H, m), 1.36, (6H, d), 0.97, (3H, t). MS 461, [MH$^+$]. LC retention time 3.94 min.

Biological Data

The ability of the compounds of the invention to bind to EP4 receptors has been demonstrated in the Human EP$_4$ Scintillation Proximity Assay.

Quantification of radioligand binding by scintillation proximity assay (SPA) is a long-established principle. Briefly, the affinity of novel compounds for a receptor is assessed by the specific competition between known quantities of radiolabelled ligand and novel compound for that receptor. Increasing concentrations of novel compound reduce the amount of radiolabel that binds to the receptor. This gives rise to a diminishing scintillation signal from SPA beads coated with membranes that bear the receptor. The signal may be detected with a suitable scintillation counter and the data generated may be analysed with suitable curve-fitting software.

The human EP$_4$ SPA assay (hereafter referred to as 'the assay') utilises membranes prepared from Chinese Hamster Ovary (CHO cells) infected with Semliki Forest Virus (SFV). Genetically engineered SFV-1 viral particles containing the genetic sequence of the human EP4 receptor were used to infect CHO cells resulting in expression of the receptor protein in cellular membranes. Cells washed free of media are homogenised in a pH-buffered medium containing peptidase inhibitors. A suitable buffer is of the following composition: 50 mM HEPES, 1 mM EDTA, 25 μg/ml bacitracin, 100 μM leupeptin, 1 mM PMSF, 2 μM Pepstatin A, pH adjusted to 7.4 with KOH. Following removal of cell debris by a low-speed centrifugation, a pellet of membranes is prepared by a high-speed (48000 g) centrifugation of the resulting supernatant. Membrane suspensions such as that described may be stored at −80° C. until used.

For assay, membranes expressing human $EP_4$ receptors are diluted in a pH-buffered medium and mixed with SPA beads coated with a suitable substance to facilitate the adhesion of membranes to the beads. The concentrations of membrane protein and SPA beads chosen should result in SPA binding signal of at least 300 corrected counts per minute (CCPM) when tritiated radioligand at a concentration close to its $K_d$ (affinity value) is combined with the mixture. Non-specific binding (nsb) may be determined by competition between the radiolabelled ligand and a saturating concentration of unlabelled ligand. In order to quantify the affinity of novel EP4 receptor ligands, compounds are diluted in a stepwise manner across the wells of a 96-well plate. Radioligand, novel compound, and unlabelled ligand are then added to a 96-well plate suitable for the measurement of SPA binding signals prior to the addition of bead/membrane mixture to initiate the binding reaction. Equilibrium may be achieved by incubation at room temperature for 120 minutes prior to scintillation counting. The data so generated may be analysed by means of a computerised curve-fitting routine in order to quantify the concentration of compound that displaces 50% of the specific radioligand binding ($IC_{50}$). The affinity ($pK_i$) of the novel compound may be calculated from the $IC_{50}$ by application of the Cheng-Prusoff correction. Suitable reagents and protocols are: reaction buffer containing 50 mM HEPES, 10 mM $MgCl_2$, pH adjusted to 7.4 with KOH; SPA beads coated with wheatgerm agglutinin; 1.25 nM [$^3$H]-prostaglandin $E_2$ as radioligand; 10 μM prostaglandin $E_2$ as unlabelled ligand; a three-fold dilution series of novel compound starting at 10 μM and ending at 0.3 nM is adequate.

The following examples have a $pK_i$ of 6.0 or greater at EP4 receptors as determined using the above-mentioned procedure:
1, 4, 5, 8, 9, 12, 13, 14, 17.

The invention claimed is:

1. A compound of formula (I) or a pharmaceutically acceptable salt thereof;

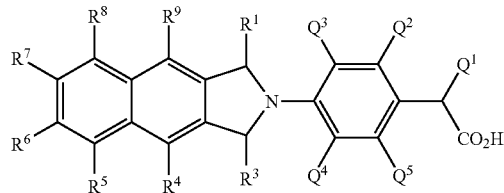

wherein,
$R^1$ is =O or hydrogen;
$R^3$ is =O, hydrogen, $C_{1-6}$ alkyl, $C_{1-6}$ dialkyl, or a 5- or 6-membered aryl;
$R^4$ and $R^9$ are the same or different and represent hydrogen or $C_{1-6}$ alkoxy;
$R^5$ and $R^8$ are hydrogen, or $CF_3$;
$R^6$ and $R^7$ are the same or different and represent hydrogen, $C_{1-6}$ alkyl, $C_{1-6}$ alkoxy, halogen, $NO_2$ or $CF_3$;
$Q^1$ is hydrogen, $C_{1-6}$ alkoxy, NHAc, or $NR_2^{10}$, where $R^{10}$ is hydrogen or $C_{1-6}$ alkyl;
$Q^2$, $Q^3$, $Q^4$ and $Q^5$ are the same or different and represent hydrogen, $C_{1-6}$ alkyl, $C_{1-6}$ alkoxy, halogen or a 5- or 6-membered aryl;
with the proviso that the compound [4-(4,9-diethoxy-1-oxo-1,3-dihydro-2H-benzo[f]isoindol-2-yl)phenyl]acetic acid are excluded.

2. A compound according to claim 1, which is selected from the group consisting of:
[4-(4,9-dimethoxy-1-oxo-1,3-dihydro-2H-benzo[f]isoindol-2-yl)phenyl]acetic acid;
[4-(4,9-diethoxy-1,3-dihydro-2H-benzo[f]isoindol-2-yl)phenyl]acetic acid;
[4-(4,9-di-isopropoxy-1-oxo-1,3-dihydro-2H-benzo[f]isoindol-2-yl)phenyl]acetic acid;
[4-(4,9-dipropoxy-1-oxo-1,3-dihydro-2H-benzo[f]isoindol-2-yl)phenyl]acetic acid;
[4-(4,9-dibutoxy-1-oxo-1,3-dihydro-2H-benzo[f]isoindol-2-yl)phenyl]acetic acid;
[4-(4,9-dihexyloxy-1-oxo-1,3-dihydro-2H-benzo[f]isoindol-2-yl)phenyl]acetic acid;
[4-(4-ethoxy-9-isopropoxy-1-oxo-1,3-dihydro-2H-benzo[f]isoindol-2-yl)phenyl]acetic acid;
[4-(9-ethoxy-4-isopropoxy-1-oxo-1,3-dihydro-2H-benzo[f]isoindol-2-yl)phenyl]acetic acid;
[4-(9-isopropoxy-4-propoxy-1-oxo-1,3-dihydro-2H-benzo[f]isoindol-2-yl)phenyl]acetic acid;
[4-(4-isopropoxy-9-propoxy-1-oxo-1,3-dihydro-2H-benzo[f]isoindol-2-yl)phenyl]acetic acid;
[4-(4-hexyloxy-9-isopropoxy-1-oxo-1,3-dihydro-2H-benzo[f]isoindol-2-yl)phenyl]acetic acid;
[4-(9-hexyloxy-4-isopropoxy-1-oxo-1,3-dihydro-2H-benzo[f]isoindol-2-yl)phenyl]acetic acid;
[4-(4-methoxy-1-oxo-1,3-dihydro-2H-benzo[f]isoindol-2-yl)phenyl]acetic acid;
[4-(4,9-diethoxy-1,3-dioxo-1,3-dihydro-2H-benzo[f]isoindol-2-yl)phenyl]acetic acid;
[4-(4,9-di-isopropoxy-1,3-dioxo-1,3-dihydro-2H-benzo[f]isoindol-2-yl)phenyl]acetic acid;
[4-(4,9-dipropoxy-1,3-dioxo-1,3-dihydro-2H-benzo[f]isoindol-2-yl)phenyl]acetic acid;
[4-(4,9-dibutoxy-1,3-dioxo-1,3-dihydro-2H-benzo[f]isoindol-2-yl)phenyl]acetic acid;
[4-(4,9-dihexyloxy-1,3-dioxo-1,3-dihydro-2H-benzo[f]isoindol-2-yl)phenyl]acetic acid;
[4-(4-ethoxy-9-isopropoxy-1,3-dioxo-1,3-dihydro-2H-benzo[f]isoindol-2-yl)phenyl]acetic acid;
[4-(9-isopropoxy-4-propoxy-1,3-dioxo-1,3-dihydro-2H-benzo[f]isoindol-2-yl)phenyl]acetic acid; and
[4-(4-butoxy-9-isopropoxy-1,3-dioxo-1,3-dihydro-2H-benzo[f]isoindol-2-yl)phenyl]acetic acid.

3. A pharmaceutical composition comprising a compound of claim 1 and a pharmaceutically acceptable carrier or diluent thereof.

* * * * *